United States Patent
Dakka et al.

(10) Patent No.: US 9,512,296 B2
(45) Date of Patent: Dec. 6, 2016

(54) AROMATIC ACYLATION WITH CYCLIC ANHYDRIDE FOR PLASTICIZER PRODUCTION

(71) Applicant: ExxonMobil Research and Engineering Company, Annandale, NJ (US)

(72) Inventors: Jihad Mohammed Dakka, Whitehouse Station, NJ (US); Edmund John Mozeleski, Somerset, NJ (US); Lisa Saunders Baugh, Ringoes, NJ (US); Karla Schall Colle, Magnolia, TX (US); Allen David Godwin, Seabrook, TX (US); Diana S. Smirnova, High Bridge, NJ (US); Jorg Friedrich Wilhelm Weber, Houston, TX (US); Stephen Zushma, Clinton, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 312 days.

(21) Appl. No.: 14/100,768

(22) Filed: Dec. 9, 2013

(65) Prior Publication Data

US 2014/0100384 A1 Apr. 10, 2014

Related U.S. Application Data

(62) Division of application No. 12/840,715, filed on Jul. 21, 2010, now Pat. No. 8,604,114.

(51) Int. Cl.
C08K 5/12 (2006.01)
C07C 51/31 (2006.01)
(Continued)

(52) U.S. Cl.
CPC .................. *C08K 5/12* (2013.01); *C07C 51/31* (2013.01); *C07C 67/08* (2013.01); *C07C 67/31* (2013.01);
(Continued)

(58) Field of Classification Search
CPC ............ C08K 5/12; C08K 5/10; C07C 67/08; C07C 67/738; C07C 51/31; C07C 69/73; C07C 69/732; C07C 67/31; C07C 2102/10
(Continued)

(56) References Cited

U.S. PATENT DOCUMENTS 1,909,092 A 5/1933 Brunson
2,233,513 A 3/1941 Brunson
(Continued)

FOREIGN PATENT DOCUMENTS

JP 44-36754 B2 * 1/2010 ............. C07C 67/00
WO 9932427 7/1999
(Continued)

OTHER PUBLICATIONS

Shintou et al., machine English translation of JP 44-36754 (Jan. 2010).*
(Continued)

*Primary Examiner* — Michael Pepitone
*Assistant Examiner* — Jessica Roswell
(74) *Attorney, Agent, or Firm* — Robert A. Migliorini

(57) ABSTRACT

Provided is a process for making non-phthalate plasticizers, by acylating an aromatic compound with a succinic anhydride to form a keto-acid, and then esterifying the keto-acid with $C_4$-$C_{13}$ OXO-alcohols to form a plasticizer compound. The aromatic rings of the aromatic compound may also be optionally hydrogenated.

4 Claims, 1 Drawing Sheet

(51) Int. Cl.
*C07C 67/08* (2006.01)
*C07C 67/31* (2006.01)
*C07C 69/73* (2006.01)
*C07C 69/738* (2006.01)
*C08K 5/10* (2006.01)
*C07C 69/732* (2006.01)

(52) U.S. Cl.
CPC .............. *C07C 69/73* (2013.01); *C07C 69/732* (2013.01); *C07C 69/738* (2013.01); *C08K 5/10* (2013.01); *C07C 2102/10* (2013.01)

(58) Field of Classification Search
USPC ......................................................... 524/359
See application file for complete search history.

(56) References Cited

U.S. PATENT DOCUMENTS

| | | | |
|---|---|---|---|
| 2,372,947 | A | 4/1945 | Gresham |
| 3,110,724 | A | 11/1963 | Woodbridge et al. |
| 5,068,393 | A * | 11/1991 | Maignan ................. C07C 57/50 514/844 |
| 6,274,756 | B1 | 8/2001 | Caers et al. |
| 6,482,972 | B1 | 11/2002 | Bahrmann et al. |
| 6,740,254 | B2 | 5/2004 | Zhou et al. |
| 6,777,514 | B2 | 8/2004 | Patil et al. |
| 7,297,738 | B2 | 11/2007 | Gosse et al. |
| 8,476,350 | B2 | 7/2013 | Dakka et al. |
| 2006/0247461 | A1 | 11/2006 | Schlosberg et al. |
| 2008/0242895 | A1 | 10/2008 | Godwin et al. |

FOREIGN PATENT DOCUMENTS

| | | |
|---|---|---|
| WO | 2003029339 | 4/2003 |
| WO | 2004046078 | 6/2004 |
| WO | 2004046078 A1 | 6/2004 |
| WO | 2009118261 A1 | 10/2009 |

OTHER PUBLICATIONS

A.D. Godwin, "Plasticizers", Applied Polymer Science 21st Century, edited by C.D. Craver and C.E. Carraher, Elsevier, 2000, pp. 157-175.

* cited by examiner

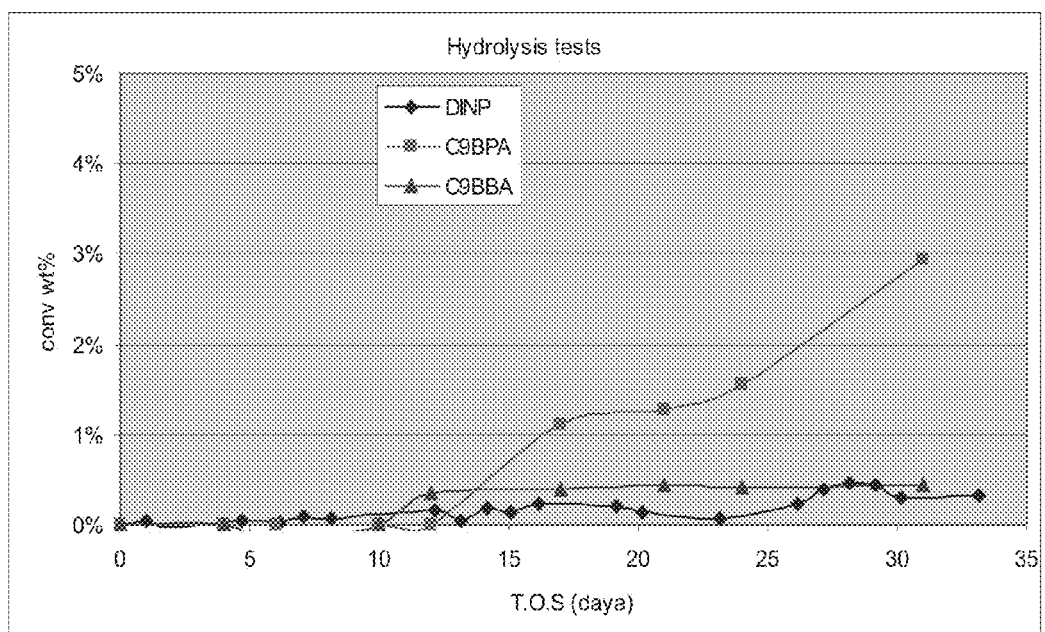

AROMATIC ACYLATION WITH CYCLIC ANHYDRIDE FOR PLASTICIZER PRODUCTION

CROSS REFERENCE TO RELATED APPLICATIONS

This application is a divisional application filed under 37 C.F.R. 1.53(b) of parent application U.S. Ser. No. 12/840,715, the entirety of which is hereby incorporated herein by reference, which claims priority to U.S. Provisional Patent Application No. 61/284,789 filed on Dec. 24, 2009, also herein incorporated by reference in its entirety.

FIELD

This disclosure is related to a potential route to non-phthalate, OXO-(di)ester plasticizers.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there has been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Patent Publication No. 2006-0247461, and U.S. Pat. No. 7,297,738.

Other suggested substitutes include esters based on benzoic acid (see, for instance, U.S. Pat. No. 6,740,254, and also co-pending, commonly-assigned, PCT Publication No. WO2009/118261A1, and polyketones, such as described in U.S. Pat. No. 6,777,514; and also co-pending, commonly-assigned, U.S. Patent Application Publication No. 2008-0242895 A1. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers. Co-pending and commonly assigned U.S. patent application Ser. No. 12/653,744, filed Dec. 17, 2009, discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

U.S. Pat. Nos. 1,909,092 and 2,233,513, both to Brunson and incorporated herein by reference, disclose esters of aryl benzoic acids of the formula R—CO—R'—COOH, wherein R and R' are aromatic nuclei, including esters derived from saturated monohydric alcohols containing three or more carbon atoms in the molecule, such as iso-propyl, butyl, isoamyl, beta-ethoxyethyl, beta-butoxyethyl, benzyl and cyclohexyl alcohols. The esters are disclosed as useful as plasticizers for nitrocellulose.

U.S. Pat. No. 2,372,947 to Gresham, incorporated herein by reference, discloses polyvinyl halide compositions containing alkyl esters of ortho-benzoyl benzoic acid, wherein the ester group is a $C_4$ to $C_{16}$ alkyl, such as butyl o-benzoyl benzoate, 2-ethylhexyl o-benzoyl benzoate, lauryl o-benzoyl benzoate, and cetyl o-benzoyl benzoate.

U.S. Pat. No. 3,110,724 to Woodbridge et al., incorporated herein by reference, discloses a process of reacting an aromatic anhydride with another aromatic compound over a catalyst and esterifying the resulting intermediate with a polyalkylene glycol to form surfactants.

Co-pending and commonly owned U.S. Provisional Patent Application Ser. No. 61/227,116, filed Jul. 21, 2009, herein incorporated by reference, discloses the esterification of keto acids derived from the acylation of aromatic compounds with cyclic anhydrides.

Thus what is needed is a method of making a general purpose non-phthalate plasticizer having and providing a plasticizer having suitable melting or chemical and thermal stability, pour point, glass transition, increased compatibility, good performance and low temperature properties.

SUMMARY

In one aspect, the present application is directed to a process for making non-phthalate plasticizers, comprising acylating an aromatic compound with a succinic anhydride to form a keto-acid, and esterifying the keto-acid with $C_4$-$C_{13}$ OXO-alcohols to form a plasticizer compound. The aromatic compound may have one or multiple rings.

In a preferred embodiment, the aromatic compound is of the formula:

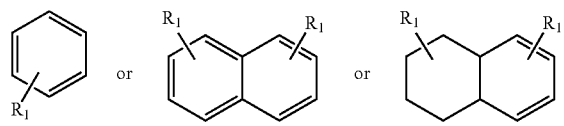

wherein $R_1$ is selected from the group consisting of H or $C_1$-$C_9$ linear or branched alkyl, cycloalkyl, or $C_1$-$C_4$ ether and wherein there may be 1 or 2 $R_1$ groups present on the aromatic or saturated ring which may be the same or different, and the plasticizer compound is of the formula:

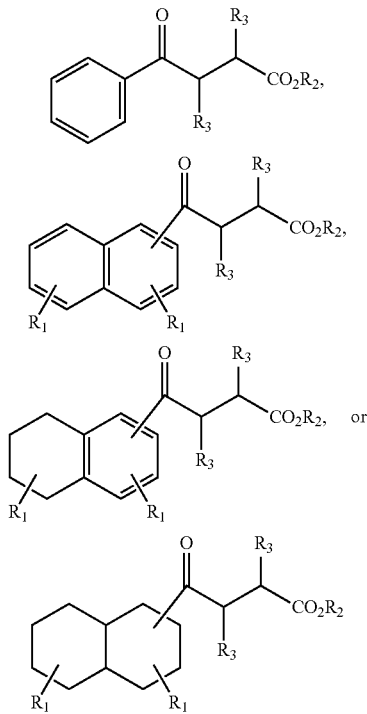

wherein $R_1$ is as set forth above, $R_2$ is the alkyl residue of the OXO-alcohols, and $R_3$ is H or $C_1$-$C_8$ linear or branched alkyl group.

In another embodiment, the acylation is catalyzed by a heterogeneous catalyst, a mixed metal oxide or a Lewis acid.

Preferably, the acylation is conducted using a stoichiometric amount of $AlCl_3$.

The process can further comprise hydrogenating one or more of the aromatic rings of the aromatic compound.

In a preferred embodiment, the process can further comprise hydrogenating the keto-group(s) of the plasticizer compound to form alcohol groups, and esterifying the alcohol groups with $C_4$ to $C_{13}$ linear or OXO-acids to form plasticizer compounds of the formula:

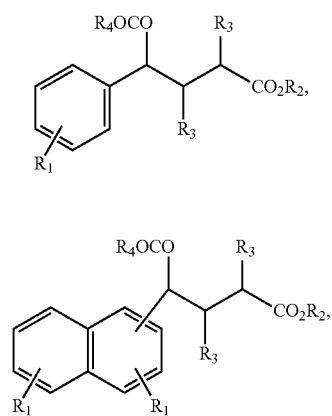

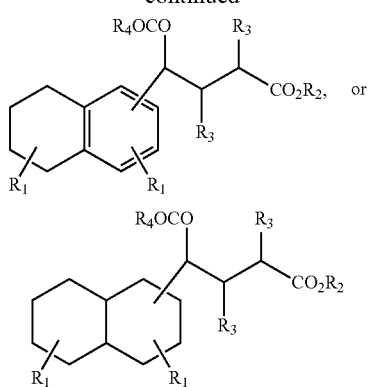

wherein $R_4$ is the alkyl residue of said linear or OXO-acids. Another embodiment of the disclosure is directed to a plasticizer compound of the formula:

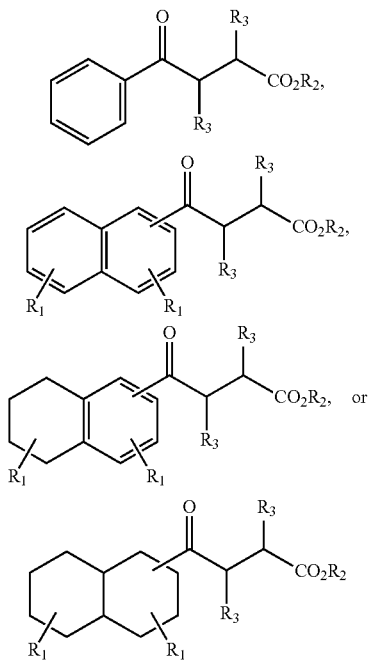

wherein $R_1$ is selected from the group consisting of H, $C_1$-$C_9$ linear or branched alkyl, cycloalkyl, or $C_1$-$C_4$ ether, and $R_2$ is the alkyl residue of $C_4$ to $C_{13}$ OXO-alcohols and wherein there may be 1 or 2 $R_1$ groups present on the aromatic or saturated ring which may be the same or different. $R_3$ is H or $C_1$-$C_8$ linear or branched alkyl group.

Additionally, the present disclosure is directed to a plasticizer compound of the formula:

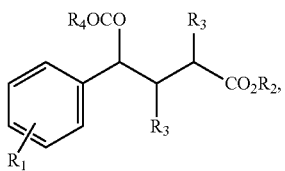

-continued

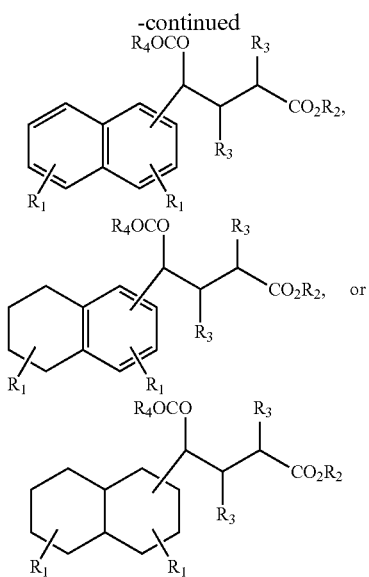

wherein $R_1$ is selected from the group consisting of H, $C_1$-$C_9$ linear or branched alkyl, cycloalkyl, or $C_1$-$C_4$ ether, wherein there may be 1 or 2 $R_1$ groups present on the aromatic or saturated ring which may be the same or different, $R_2$ is the alkyl residue of $C_4$ to $C_{13}$ OXO-alcohols, $R_3$ is H or $C_1$-$C_8$ linear or branched alkyl group, and $R_4$ is the alkyl residue of $C_4$ to $C_{13}$ linear or OXO-acids.

In another embodiment, the present disclosure is directed to a composition comprising a polymer and a plasticizer of the formula:

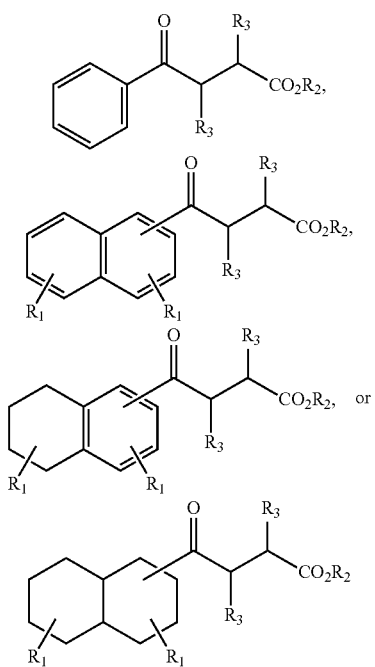

wherein $R_1$ is selected from the group consisting of H, $C_1$-$C_9$ linear or branched alkyl, cycloalkyl, or $C_1$-$C_4$ ether, wherein there may be 1 or 2 $R_1$ groups present on the aromatic or saturated ring which may be the same or different, $R_2$ is the alkyl residue of $C_4$ to $C_{13}$ OXO-alcohols, and $R_3$ is H or $C_1$-$C_8$ linear or branched alkyl group.

Conveniently, the composition contains a polymer selected from the group consisting of vinyl chloride resins, polyesters, polyurethanes, ethylene-vinyl acetate copolymer, rubbers, poly(meth)acrylics and combinations thereof, preferably polyvinylchloride.

In another embodiment, the disclosure is directed to a composition comprising a polymer and a plasticizer of the formula:

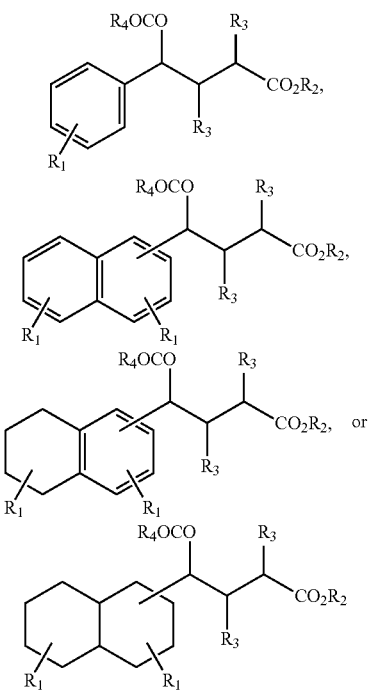

wherein $R_1$ is selected from the group consisting of H, $C_1$-$C_9$ linear or branched alkyl, cycloalkyl, or $C_1$-$C_4$ ether wherein there may be 1 or 2 $R_1$ groups present on the aromatic or saturated ring which may be the same or different, $R_2$ is the alkyl residue of $C_4$-$C_{13}$ OXO-alcohols, $R_3$ is H or $C_1$-$C_8$ linear or branched alkyl group, and $R_4$ is the alkyl residue of $C_4$-$C_{13}$ linear or OXO-acids.

Preferably the polymer is selected from the group consisting of vinyl chloride resins, polyesters, polyurethanes, ethylene-vinyl acetate copolymer, rubbers, poly(meth)acrylics and combinations thereof, and more preferably is polyvinylchloride.

BRIEF DESCRIPTION OF THE DRAWINGS

FIG. 1 is a graph showing a comparison of the long term stability against hydrolysis of various plasticizers (DINP=diisononyl phthalate; $C_9$BPA=OXO—$C_9$ benzoyl propionate (Ex. 18); $C_9$BBA=OXO—$C_9$ benzoyl benzoate (Ex. 3).

DETAILED DESCRIPTION

All numerical values within the detailed description and the claims herein are modified by "about" or "approximately" the indicated value, and take into account experimental error and variations that would be expected by a person having ordinary skill in the art.

There is an increased interest in developing new plasticizers that are non-phthalates and which possess good plasticizer performance characteristics but are still competitive economically. The present disclosure is directed towards non-phthalate, OXO-(di)ester plasticizers that can be made from low cost feeds and employ fewer manufacturing steps in order to meet economic targets. The process for making the non-phthalate plasticizers disclosed herein is to produce a single or multi ring aromatic acid, made from single or multi ring aromatic molecule acylation with a cyclic anhydride, followed by esterification of the acid with OXO $C_4$-$C_{13}$ alcohols. Two additional steps may also be optionally utilized for fine tuning plasticizer compatibility, volatility, or stability, which are: i) converting the carbonyl group to an alcohol group using hydrogenation technology and esterifying the alcohol with OXO $C_4$-$C_{13}$ acids; and ii) hydrogenating one or more of the unsaturated aromatic rings.

Branched aldehydes can be produced by hydroformylation of $C_3$-$C_{12}$ olefins; in turn, some of these olefins have been produced by propylene and/or butene oligomerization over solid phosphoric acid or zeolite catalysts. The resulting $C_4$-$C_{13}$ aldehydes can then be recovered from the crude hydroformylation product stream by fractionation to remove unreacted olefins. These $C_4$-$C_{13}$ aldehydes can then hydrogenated to alcohols (OXO-alcohols) or oxidized to acids (OXO-acids). Single carbon number acids or alcohols can be used in the esterification of the aromatic acids described above, or differing carbon numbers can be used to optimize product cost and performance requirements. The "OXO" technology will provide cost advantaged alcohols and acids. Other options are considered, such as hydroformylation of $C_4$-olefins to $C_5$-aldehydes, followed by hydrogenation to $C_5$-alcohols, or aldehyde dimerization followed by hydrogenation or oxidation to $C_{10}$-alcohols or acids.

The resulting $C_4$-$C_{13}$ OXO-alcohols (and acids) may be used individually, or together in mixtures to make mixed carbon number materials to make esters for use as plasticizers. The mixing of carbon numbers and levels of branching may be required to achieve the desired compatibility with PVC for the respective aromatic acid used for the polar end of the plasticizer, and to meet other plasticizer performance properties. The feed can be propylene, butenes, pentenes, hexenes, heptenes, octenes or nonenes as the starting olefins. The selected from $C_4$-$C_{13}$ OXO-acids or alcohols have an average branching of from about 0.2 to about 4.0 branches per molecule. Average branching is determined by NMR. The average branching of the alkyl groups incorporated into the plasticizers as the residues of the OXO-acid or alcohol reagents may range from 0.2 to 4.0, or 0.5 to 3.5, or 1.0 to 3.0, or 1.5 to 2.5 branches per residue.

An "OXO-ester" is a compound having at least one functional ester moiety within its structure derived from esterification of either an acid or alcohol compound with an OXO-alcohol or OXO-acid, respectively.

An "OXO-alcohol" is an organic alcohol, or mixture of organic alcohols, which is prepared by hydroformylating an olefin, followed by hydrogenation to form the alcohols. Typically, the olefin is formed by light olefin oligomerization over heterogeneous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety.

An "OXO-acid" is an organic acid, or mixture of organic acids, which is prepared by hydroformylating an olefin, followed by oxidation to form the acids. Typically, the olefin is formed by light olefin oligomerization over heterogeneous acid catalysts, which olefins are readily available from refinery processing operations. The reaction results in mixtures of longer-chain, branched olefins, which subsequently form longer-chain, branched acids.

Alternatively, the OXO-acids or OXO-alcohols can be prepared by aldol condensation of shorter-chain aldehydes to form longer chain aldehydes, as described in U.S. Pat. No. 6,274,756, followed by oxidation or hydrogenation to form the OXO-acids or OXO-alcohols, respectively.

Tables 1A and 1B below provide branching characteristics for typical OXO-alcohols and OXO-acids, measured by $^{13}C$ NMR.

TABLE 1A $^{13}C$ NMR Branching Characteristics of Typical OXO-Alcohols.

| OXO-Alcohol | Avg. Carbon No. | % of α-Carbons w/Branches[a] | β-Branches per Molecule[b] | Total Methyls per Molecule[c] | Pendant Methyls per Molecule[d] | Pendant Ethyls per Molecule |
|---|---|---|---|---|---|---|
| $C_4$[e] | 4.0 | 0 | 0.35 | 1.35 | 0.35 | 0 |
| $C_5$[f] | 5.0 | 0 | 0.30 | 1.35 | 0.35 | 0 |
| $C_6$ | — | — | — | — | — | — |
| $C_7$ | 7.3 | 0 | 0.15 | 1.96 | 0.99 | 0.04 |
| $C_8$ | 8.6 | 0 | 0.09 | 3.0 | 1.5 | — |
| $C_9$ | 9.66 | 0 | 0.09 | 3.4 | — | — |
| $C_{10}$ | 10.2 | 0 | 0.16 | 3.2 | — | — |
| $C_{12}$ | 12.2 | 0 | — | 4.8 | — | — |
| $C_{13}$ | 13.1 | 0 | — | 4.4 | — | — |

— Data not available.

[a]-COH carbon.

[b]Branches at the-$CCH_2OH$ carbon.

[c]This value counts all methyl groups, including $C_1$ branches, chain end methyls, and methyl endgroups on $C_2+$ branches.

[d]$C_1$ branches only.

[e]Calculated values based on an assumed molar isomeric distribution of 65% n-butanol and 35% isobutanol (2-methylpentanol).

[f]Calculated values based on an assumed molar isomeric distribution of 65% n-pentanol, 30% 2-methylbutanol, and 5% 3-methylbutanol.

TABLE 1B $^{13}$C NMR Branching Characteristics of Typical OXO-Acids.

| OXO-Acid | Average Carbon No. | Pendant Methyls[a] | Total Methyls[b] | Pendant Ethyls | % Carbonyls α to Branch[c] |
|---|---|---|---|---|---|
| $C_4$[d] | 4.0 | 0.35 | 1.35 | 0 | 35 |
| $C_5$[e] | 5.0 | 0.35 | 1.35 | 0 | 30 |
| $C_6$ | — | — | — | — | — |
| $C_7$ | 6.88-7.92 | 0.98-1.27 | 1.94-2.48 | 0.16-0.26 | 11.3-16.4 |
| $C_8$ | 8.1-8.3 | — | 2.7 | — | 12-15 |
| $C_9$ | 9.4 | — | n/a | — | 12 |
| $C_{10}$ | 10.2 | — | n/a | — | 12 |
| $C_{12}$ | — | — | — | — | — |
| $C_{13}$ | 12.5 | — | 4.4 | — | 11 |

— Data not available.
[a]$C_1$ Branches only.
[b]Includes methyls on all branch lengths and chain end methyls.
[c]The "alpha" position in the acid nomenclature used here is equivalent to the alcohol "beta" carbon in Table 1A.
[d]Calculated values based on an assumed molar isomeric distribution of 65% n-butanoic acid and 35% isobutanoic acid (2-methylpentanoic acid).
[e]Calculated values based on an assumed molar isomeric distribution of 65% n-pentanoic acid, 30% 2-methylbutanoic acid, and 5% 3-methylbutanoic acid.

"Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process.

"Hydrogenating" or "hydrogenation" is addition of hydrogen ($H_2$) to a double-bonded functional site of a molecule, such as in the present case, addition of hydrogen to the ketone functionality of the plasticizer to give an alcohol functionality, or to the aldehyde moieties of an OXO-aldehyde, to form the corresponding alcohol. Hydrogenation may also be the addition of hydrogen ($H_2$) to one or more aromatic rings of the plasticizer or a precursor thereof, to form a saturated cyclic structure. Conditions for hydrogenation are well known in the art and include, but are not limited to temperatures of 0-300° C., pressures of 1-500 atmospheres, and the presence of homogeneous or heterogeneous hydrogenation catalysts such as Pt/C, Pt/Al$_2$O$_3$ or Pd/Al$_2$O$_3$.

"Esterifying" or "esterification" is reaction of a carboxylic acid moiety with an organic alcohol moiety to form an ester linkage. Esterification conditions are well-known in the art and include, but are not limited to, temperatures of 0-300° C., and the presence or absence of homogeneous or heterogeneous esterification catalysts such as Lewis or Brønsted acid catalysts.

In general, for every polymer to be plasticized, a plasticizer is required with the correct balance of solvating properties, volatility and viscosity to have acceptable plasticizer compatibility with the resin. In particular, if the 20° C. kinematic viscosity is higher than 150 mm$^2$/sec as measured by the appropriate ASTM test, or alternately if the 20° C. cone-and-plate viscosity is higher than 150 cP, this will affect the plasticizer processability during formulation, and may require heating the plasticizer to ensure good transfer during storage and mixing of the polymer and the plasticizer. Volatility is also a very critical factor which affects the long-term plasticizer formulation stability. Higher volatility plasticizers can migrate from the plastic resin matrix and cause damage to the article. The plasticizer volatility in a resin matrix can be roughly predicted by neat plasticizer weight loss at 220° C. using Thermogravimetric Analysis.

The present disclosure discloses unexpected structure-property relationships arising from the addition of specific substituents to the aromatic ring of the aromatic acid fragment of the plasticizer molecule. These manipulations allow for the preparation of novel ketoester plasticizers having improved volatility-viscosity balances.

One potential route to non-phthalate plasticizers is by acylating an alkyl aromatic acid with a succinic anhydride of the general structure

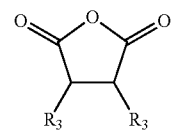

wherein $R_3$ can be H or $C_1$-$C_8$ alkyl, (ex: methylsuccinic anhydride, isopropylsuccinic anhydride, n-butylsuccinic anhydride, n-octylsuccinic anhydride) followed by esterification of the free acid group with an OXO-alcohol. When there are two $R_3$ groups present on the anhydride, they may also form a fused $C_6$ aromatic ring, as in phthalic anhydride. Non-limiting exemplary aromatic compounds for acylation are as follows:

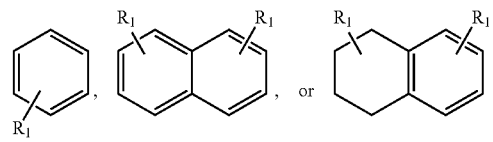

wherein $R_1$ is selected from the group consisting of H, $C_1$-$C_9$ linear or branched alkyl, cycloalkyl, or $C_1$-$C_4$ ether and wherein there may be 1 or 2 $R_1$ groups present on the aromatic or saturated ring which may be the same or different.

The general reaction mechanism is illustrated as follows:

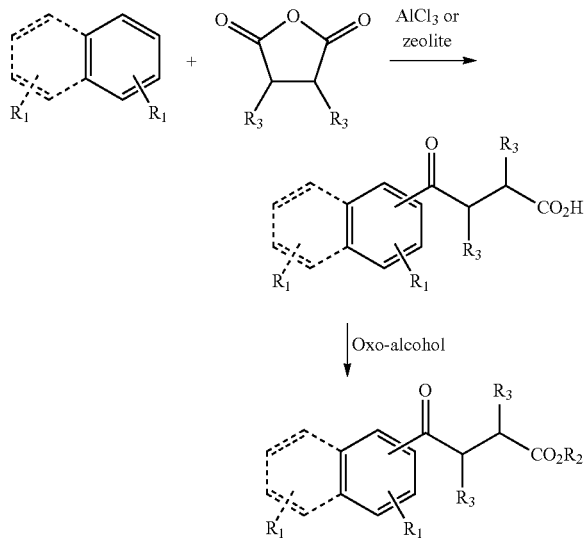

In the above structure, $R_1$ is selected from the group consisting of H, $C_1$-$C_9$ linear or branched alkyl, cycloalkyl, or $C_1$-$C_4$ ether, wherein there may be 1 or 2 $R_1$ groups present on the aromatic or saturated ring which may be the same different, $R_2$ is the alkyl residue of $C_4$-$C_{13}$ OXO-alcohols, and $R_3$ is H or a $C_1$-$C_8$ linear or branched alkyl group.

Following the esterification step with the OXO-alcohol (or, alternately, following the acylation step with the cyclic anhydride), one or more of the aromatic rings of the aromatic compounds depicted above may also be hydrogenated using typical hydrogenation catalysts known in the art, and in particular the platinum group metals, such as palladium, ruthenium, or combinations thereof on a silica, carbon, or alumina support at a metals loading level on the support of 0.1-10, or 0.5-7, or 1-5 wt. %. The hydrogenation conditions may be at a temperature of 80-300, or 100-280, or 150-250° C. at a pressure of 100-3000, or 500-2500, or 1000-2000 psig. Hence, the plasticizer compound depicted above may be unsaturated, partially saturated, or fully saturated depending upon hydrogenation of the one or more aromatic rings of the compound. The general mechanism is illustrated as follows:

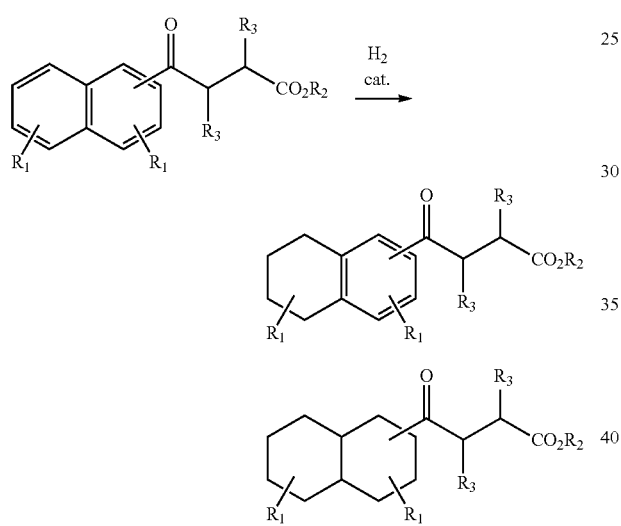

An extra two steps may then be optionally used to convert the carbonyl group of the above products to an alcohol group using hydrogenation technology, and then the alcohol may be esterified per the schematic below:

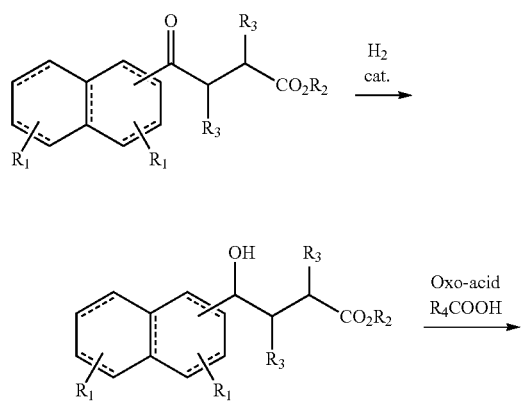

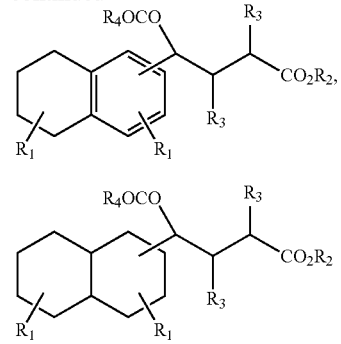

The general reaction mechanism above as broadened to include both single and multi-ring aromatic substrates is illustrated as follows, wherein the OXO-diester can be formed by hydrogenating the remaining carbonyl group to form an hydroxyl moiety, followed by esterification with an OXO-acid.

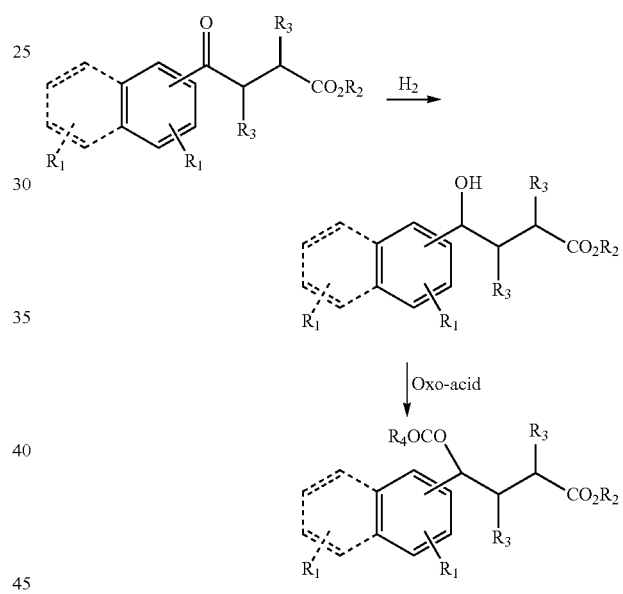

In the above structure, $R_1$ is selected from the group consisting of H, $C_1$-$C_9$ linear or branched alkyl, cycloalkyl, or $C_1$-$C_4$ ether wherein there may be 1 or 2 $R_1$ groups present on the aromatic or saturated ring which may be the same or different, $R_2$ is the alkyl residue of $C_4$-$C_{13}$ OXO-alcohols, $R_3$ is H or $C_1$-$C_8$ linear or branched alkyl group, and $R_4$ is the alkyl residue of $C_4$-$C_{13}$ linear or OXO-acids.

Following (or, alternately, preceding) the esterification step with the OXO-acid, one or more of the aromatic rings of the aromatic compounds depicted above may also be hydrogenated using typical hydrogenation catalysts known in the art, and in particular the platinum group metals, such as palladium, ruthenium, or combinations thereof on a silica, carbon, or alumina support at a metals loading level on the support of 0.1-10, or 0.5-7, or 1-5 wt. %. The hydrogenation conditions may be at a temperature of 80-300, or 100-280, or 150-250° C. at a pressure of 100-3000, or 500-2500, or 1000-2000 psig. Hence, the plasticizer compound depicted above may be unsaturated, partially saturated, or fully saturated depending upon hydrogenation of the one or more aromatic rings of the compound. The general mechanism is illustrated as follows:

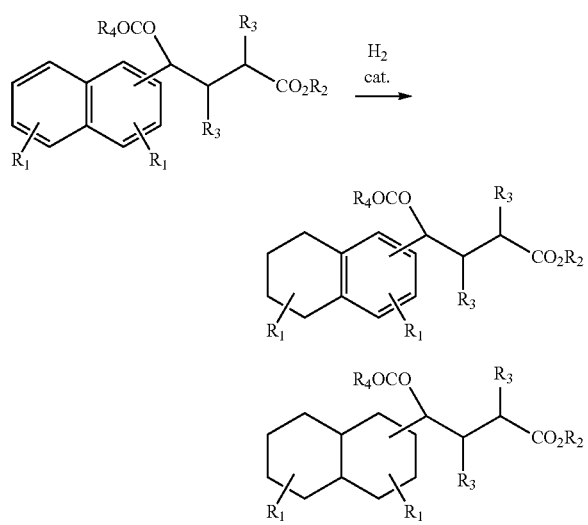

The same acylation, hydrogenation, and esterification chemistry that is applied hereinabove could be also used for already partially hydrogenated multi-ring molecules, and with separate or simultaneous hydrogenation steps (for example, the overall reaction scheme shown below):

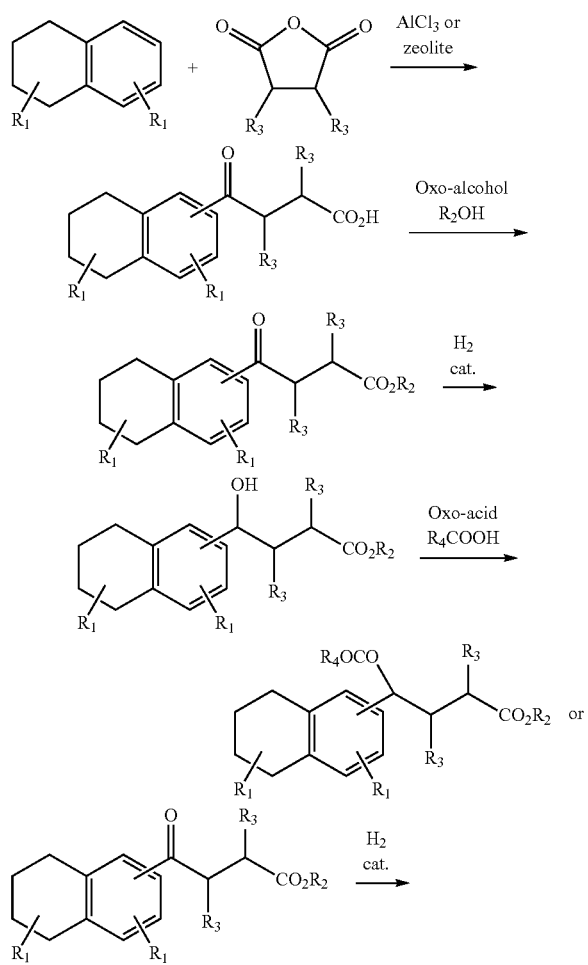

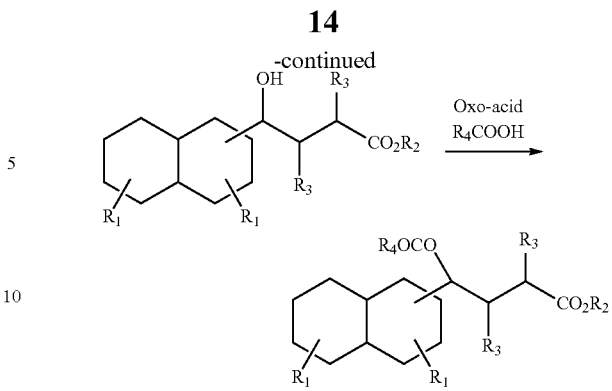

As discussed above, the resulting $C_4$-$C_{13}$ acids or alcohols can be used individually or together in acid mixtures or alcohol mixtures having different chain lengths, to make mixed carbon number esters to be used as plasticizers. This mixing of carbon numbers and levels of branching can be advantageous to achieve the desired compatibility with PVC for the respective polyol or polyacid used for the polar moiety end of the plasticizer, and to meet other plasticizer performance properties. The selected from $C_4$-$C_{13}$ acids or alcohols have an average branching of from about 0.2 to about 4.0 branches per molecule. Average branching is determined by NMR. The average branching of the alkyl groups incorporated into the plasticizers as the residues of the acid or alcohol reagents ranges from 0.2-4.0, or 0.5-3.5, or 1.0-3.0, or 1.5-2.5 branches per residue. The starting olefin feed can be $C_3{=}$, butenes, $C_5{=}$, $C_6{=}$, $C_7{=}$, $C_8{=}$ or $C_9{=}$.

We have found that when $C_4$-$C_{13}$ OXO-alcohols, OXO-acids or linear acids are used as reactants for the esterification reactions described above, the resulting OXO-esters are in the form of relatively high-boiling liquids (having low volatility), which are readily incorporated into polymer formulations as plasticizers.

EXAMPLES

General Procedure for Esterification

Into a 4-necked 500 mL round bottom flask equipped with an air stirrer, thermometer, $N_2$ inductor, Dean-Stark trap and chilled water cooled condenser were added the amounts of carboxylic acid (commercially purchased benzoyl and alkylbenzoyl benzoic acids) and alcohol specified in the following Examples. The Dean-Stark trap was filled with additional alcohol. Toluene and/or xylenes were optionally also added to control the temperature and to provide adequate reflux for water removal. The contents of the flask were stirred at the specified temperature for the specified time and water was collected in the Dean-Stark trap. The crude reaction mixture was optionally washed with a 3 wt % NaOH solution to remove residual acid prior to vacuum distillation to remove excess alcohol, and/or treated with 2 wt % decolorizing charcoal by stirring at room temperature for 2 hours, followed by double filtration to remove the charcoal. In some examples the product (rather than only residual alcohol) was distilled overhead. The specific reaction conditions and product workup are indicated in the following tables and examples. The general esterification reaction is shown in Equation 1, below. The product purity was evaluated by gas chromatography (GC) analysis, conducted using a Hewlett-Packard 5890 GC equipped with a HP6890 autosampler, a HP flame-ionization detector, and a J&W Scientific DB-1 30 meter column (0.32 micrometer inner diameter, 1 micron film thickness, 100% dimethylpolysiloxane coating). The initial oven temperature was 60° C.; injector temperature 290° C.; detector temperature 300° C.; the temperature ramp rate from 60-300° C. was 10° C./minute with a hold at 300° C. for 14 minutes. The calculated %'s reported for products were obtained from peak area, with an FID detector uncorrected for response factors.

Equation 1

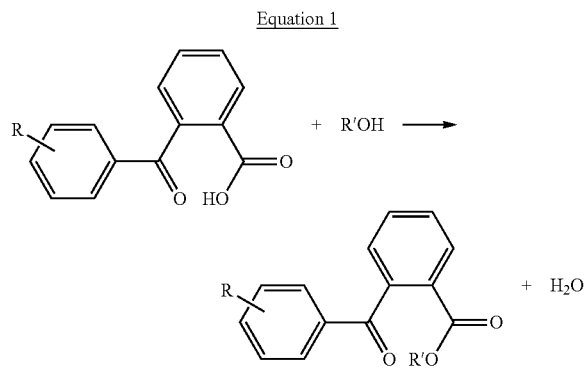

(R is equivalent to $R_1$, and R' is equivalent to $R_2$, as described previously)

Examples 1-8 demonstrate esterification of benzoylbenzoic and toluoylbenzoic acids with different alcohols, the results of which are set forth in Table 2, below (where R is equivalent to $R_1$ as described previously).

TABLE 2

| Ex., R | Carboxylic acid (grams, moles)[a] | Alcohol (grams, moles)[b] | Rxn Temp (° C.), Time (h) | Solvent, Workup[c] | Acid Conv. %, Product Purity (%) |
|---|---|---|---|---|---|
| 1, H | 2-BenzoylBz (191.8, 0.85) | 1.86:1 Hexanol/2-methylpentanol (173.3/1.696) | 175, 8 | None, A | 99.2, 99.8 |
| 2, H | 2-BenzoylBz (158.3, 0.7) | 2-Ethylhexanol (182.23, 1.4) | 210, 4 | None, A | 99.0, 99.6 |
| 3, H | 2-BenzoylBz (155.5, 0.6874) | OXO-$C_9$ (198.82, 1.3748) | 220, 8 | None, A | 93.8, 99.4 |
| 4, H | 2-BenzoylBz (118.9, 0.526) | Nonanol (151.64, 1.05) | 220, 5 | None, A | 97.8, 99.6 |
| 5, Me | 2-(4-Toluoyl)Bz (155.0, 0.6464) | 1.86:1 Pentanol/2-methylbutanol (113.9, 1.291) | 150, 9 | None, B | 99.0, 99.2 |
| 6, Me | 2-(4-Toluoyl)Bz (150.0, 0.625) | 1.843:1 Hexanol/2-methylpentanol (128, 1.25) | 170, 5.5 | None, B | NA, 98.7 |
| 7, Me | 2-(4-Toluoyl)Bz (116.25, 0.5) | 2-Ethylhexanol (126.21, 0.9696) | 210, 6 | None, B | 95.6, 97.4 |
| 8, Me | 2-(4-Toluoyl)Bz (115.1, 0.48) | OXO-$C_9$ (138.6, 0.96) | 220, 4 | None, B | 90.1, 99.6 |

[a]Bz = Benzoic acid
[b]Ratios of acids are molar ratios.
[c]A = Distilled off excess alcohol only; B = distilled product perature and cooled to −130° C. at 10° C./min and analyzed on heating to 75° C. at a rate of 10° C./min. $T_g$s given are midpoints of the second heats (unless only one heat cycle was performed, in which case the first heat $T_g$, which is typically in very close agreement, is given). Kinematic Viscosity (KV) was measured at 20° C. according to ASTM D-445-20, the disclosure of which is incorporated herein by reference, or as footnoted in the Tables.

TABLE 3

| Ex., R, R' | TGA 1% Wt Loss (° C.) | TGA 5% Wt Loss (° C.) | TGA 10% Wt Loss (° C.) | TGA Wt Loss, 220° C. (%) | DSC $T_g$ (° C.) | KV (20° C., mm²/sec) |
|---|---|---|---|---|---|---|
| 1, H, $C_6$ | 155.0 | 187.5 | 202.3 | 21.3 | −60[a] | 309.69 |
| 2, H, 2EH[f] | 167.1 | 196.7 | 211.1 | 14.9 | −61.3 | 451.60 |
| 3, H, $C_9$ | 173.3 | 204.3 | 219.0 | 10.4 | −58.1 | 434.47 |
| 4, H, n-$C_9$ | 178.4 | 208.7 | 223.7 | 8.5 | −68.9[b] | 184.6 |
| 5, Me, $C_5$ | 157.8 | 189.9 | 204.8 | 19.4 | −51.4[c] | 784.93 |
| 6, Me, $C_6$ | 161.3 | 194.4 | 210.5 | 14.7 | −54.4 | 556.6 |
| 7, Me, EH[f] | 171.0 | 202.9 | 217.6 | 11.1 | −56.8[e] | —[d] |
| 8, Me, $C_9$ | 177.4 | 214.1 | 229.5 | 6.5 | −53.9 | 775.38 |

— Data not taken.
[a]2nd small apparent $T_g$, 36.3° C.
[b]Small melting transition, 54.7° C.
[c]Small unidentified exotherm in both 1st and 2nd heats, ~−18 C.
[d]Sample was noted as a mixture of solid and liquid.
[e]2nd small potential $T_g$, 50.4° C.; small melting transition, 22.5° C.;
[f]2-ethylhexyl.

Table 3 (where R is equivalent to $R_1$ as described previously and R' is equivalent to $R_2$ as described previously) below provides neat properties of the benzoyl benzoic and toluoyl benzoic acid esters prepared in Examples 1-8. Thermogravimetric Analysis (TGA) was conducted using a TA Instruments AutoTGA 2950HR instrument (25-600° C., 10° C./min, under 60 cc $N_2$/min flow through furnace and 40 cc $N_2$/min flow through balance; sample size 10-20 mg). Differential Scanning Calorimetry (DSC) was also performed, using a TA Instruments 2920 calorimeter fitted with a liquid $N_2$ cooling accessory. Samples were loaded at room tem- The data in Table 3 show that, in order to decrease volatility, heavy alcohols had to be used which at the same time adversely affect viscosity. The addition of a methyl group to the benzene ring resulted in higher viscosity than without a methyl group. A different group (—$CH_2CH_2$—) separating the keto and ester functionalities was used in order to modify the volatility/viscosity balance. The synthesis of benzoyl and alkylbenzoyl propionic acids via acylation is shown in Equation 2 (where R is equivalent to $R_1$ as described previously). Those of skill in the art will recognize that any suitable acylation catalyst, such as a heterogeneous catalyst, a mixed metal oxide or a Lewis acid such as a homogeneous Lewis acid, such as $AlCl_3$, can be used to catalyze the reaction.

Equation 2

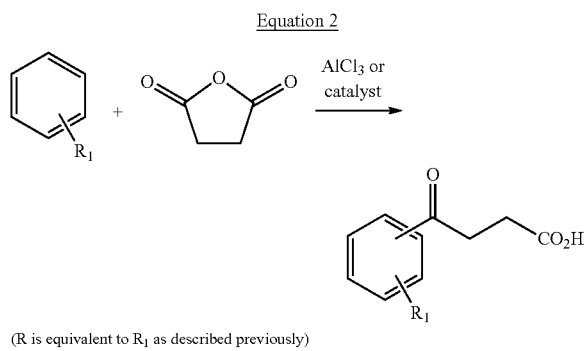

(R is equivalent to $R_1$ as described previously)

Representative Procedure for the Synthesis of Aromatic Keto Acids:

99.5 g (0.94 mole) o-xylene, 31.3 g (0.31 mole), succinic anhydride, and 190 mL nitrobenzene were placed into a 1 liter round bottom flask fitted with an addition funnel, thermometer, mechanical stirrer and nitrogen purge. The flask was cooled to 0° C., then 83.4 g (0.63 mole) of aluminum trichloride, dissolved in 350 mL nitrobenzene, was added dropwise maintaining the temperature at 0° C. After addition, the solution was stirred overnight and the temperature was allowed to reach room temperature. The solution was poured into a 2 liter beaker containing 120 mL concentrated aqueous HCl, 500 mL water, and 1000 g ice. The mixture was extracted twice with 1000 mL ethyl ether. The ether layers were combined and washed with 500 mL water, then extracted twice with 500 mL 5% aqueous potassium hydroxide. The aqueous layers were combined and washed with 500 mL ether. The aqueous layer was acidified with 100 mL concentrated aqueous HCl to precipitate the product. The product was collected by filtration and washed with 500 mL water. The product was dissolved in chloroform and the solution was dried over magnesium sulfate, filtered, and stripped of chloroform under vacuum to give 61.4 g (95.4% yield) of crude product. The product was crystallized from benzene giving a weight of 59.9 g.

A number of aromatic keto acids of the general structure shown in Equation 2 were prepared by acylation of alkylaromatics with succinic anhydride, using an aluminum trichloride reagent (rather than a heterogeneous catalyst). The following procedure is representative. The syntheses of aromatic keto acids prepared by this method are summarized in Table 4 (Examples 9-16), where R is equivalent to $R_1$ as described previously.

TABLE 4

| Ex. No. | R | Moles aromatic, anhydride, $AlCl_3$ | Crude weight (g) (yield, %) | Weight after crystallization (g) |
|---|---|---|---|---|
| 9 | Sec-butyl | 0.94, 0.31, 0.63 | 71.3 (91.7) | 59.1 |
| 10 | ethyl | 0.94, 0.31, 0.63 | 57.6 (89.5) | 33.5 |
| 11 | n-nonyl | 0.49, 0.16, 0.33 | 42.2 (88.5) | NA |
| 12 | n-hexyl | 0.94, 0.31, 0.63 | 52.0 (63.5) | NA |
| 13 | o-dimethyl | 0.94, 0.31, 0.63 | 61.4 (95.4) | 59.9 |
| 14 | m-dimethyl | 0.75, 0.25, 0.50 | 48.0 (93.1) | 28.2 |
| 15 | p-dimethyl | 0.94, 0.31, 0.63 | 58.5 (90.9) | 49.6 |
| 16 | cyclohexyl | 0.94, 0.31, 0.63 | 72.5 (89.3) | 67.6 |

NA = data not available.

The following examples illustrate the synthesis and properties of ketoesters prepared by esterification of arylpropionic acids, including the acids prepared in Table 4 and others from commercial sources. The general esterification procedure already described was used. Tables 5 and 6 (where R is equivalent to $R_1$ as described previously and in these instances is H, and R' is equivalent to $R_2$ as described previously) summarize the synthesis and performance of esters made from benzoylpropionic acid (which may be derived from benzene acylation with succinic anhydride) with and various alcohols as shown in Equation 3, below, where R' is equivalent to $R_2$ as described previously.

Equation 3

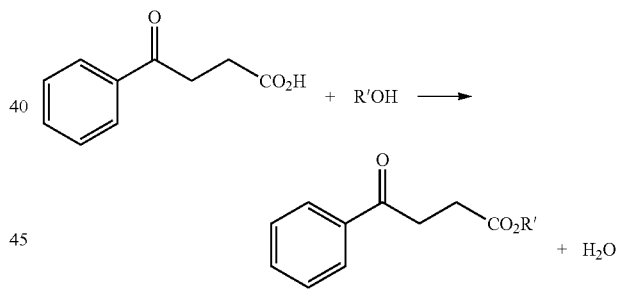

(R' is equivalent to $R_2$ as described previously)

TABLE 5

| Ex. No., R | Carboxylic acid (grams, moles)[a] | Alcohol (grams, moles) | Rxn Temp (° C.), Time (h) | Solvent, Workup[b] | Acid Conv. %, Product Purity (%) |
|---|---|---|---|---|---|
| 17, H | 3-BenzoylPr (52.5, 0.295) | 2-ethyl-1-hexanol (76.7, 0.59) | 220, 6 | None, B | 97.6, 96.6 |
| 18, H | 3-BenzoylPr (147.7, 0.829) | OXO-$C_9$ (239.7, 1.66) | 220, 5 | None, A | 98.4, 99.6 |
| 19, H | 3-BenzoylPr (189.4, 1.063) | OXO-$C_{13}$ (425.6, 2.13) | 205, 3 | Xylenes,[c] A + C | NA, 99.4 |
| 20, H | 3-BenzoylPr (43.2, 0.242) | Nonanol (85.4, 0.592) | 220, 6 | None, B | 95.7, 96.7 |

[a]Pr = Propionic
[b]A = Distilled off excess alcohol only; B = distilled product; C = treated alkyl residue with charcoal.
[c]44.6 g, 0.42 moles.

TABLE 6

| Ex. No., (R, R') | TGA 1% Wt Loss (° C.) | TGA 5% Wt Loss (° C.) | TGA 10% Wt Loss (° C.) | TGA Wt Loss, 220° C. (%) | DSC $T_g$ (° C.) | KV (20° C., mm²/sec) |
|---|---|---|---|---|---|---|
| 17, H, 2EH | 135.3 | 169.4 | 184.3 | 43.9 | −82.4[a] | 24.88 |
| 18, H, $C_9$ | 149.6 | 182.1 | 196.8 | 27.0 | −77.4 | 34.79 |
| 19, H, $C_{13}$ | 169.7 | 202.7 | 217.6 | 11.1 | −70.9 | 75.62 |
| 20, H, n-$C_9$ | 143.5 | 187.0 | 202.8 | 20.6 | None[b] | 26.1 |
| DINP | 184.6 | 215.2 | 228.5 | 6.4 | −79.1 | 96.81 |

DINP = diisononyl phthalate;
2EH = 2-ethylhexyl.
[a]Small potential melting transitions at −20.8 and 54.1 C.
[b]Strong, narrow melting transition, 26.0° C.

The data in Table 6 show that the ester made from 2-ethylhexanol (2EH) is a very volatile product. Replacing the 2EH chain with an OXO—$C_9$ chain dramatically lowers the volatility of the ester and affects the viscosity. Using a heavier alcohol ($C_{13}$) resulted in a much lower volatility and still gives a viscosity lower than that for DINP. Linear alcohols (e.g., n-nonanol) show better volatility and viscosity than OXO-branched alcohols with the same carbon number.

Another approach for decreasing volatility is to use alkylated aromatic groups to increase molecular weight, which affects volatility. Therefore, different esters were made using aromatic keto acids bearing a methyl group (this acid may be made from toluene acylation with succinic anhydride) as shown in Equation 4, below (where R' is equivalent to $R_2$ as described previously).

Equation 4

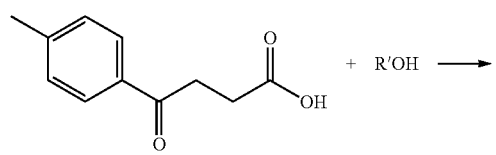

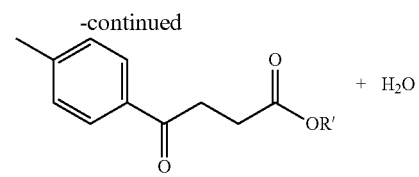

(R' is equivalent to $R_2$ as described previously)

Examples 21-24 in Table 7 (where R is equivalent to $R_1$ as described previously) demonstrate esterification of methylbenzoylpropionic acid with different alcohols. The volatility, viscosity, and glass transition properties of the neat plasticizers prepared in Examples 21-24 are set forth in Table 8 (where R is equivalent to $R_1$, and R' is equivalent to $R_2$, as described previously), below.

TABLE 7

| Ex. No., R | Carboxylic acid (grams, moles)[a] | Alcohol (grams, moles)[d] | Rxn Temp (° C.), Time (h) | Solvent, Workup[b] | Acid Conv. %, Product Purity (%) |
|---|---|---|---|---|---|
| 21, Me | 3-(4-Methyl-benzoylPr (41.4, 0.22) | 65:35 hexanol/2-methylpentanol (28.6, 0.15) | 203-210, 5 | Non, B | 92.5, 96.4 |
| 22, Me | 3-(4-Methyl-benzoylPr (69.4, 0.3612) | 2-ethyl-1-hexanol (94.1, 0.722) | 217, 7 | None, B | 97.7, 96.0 |
| 23, Me | 3-(4-Methyl-benzoylPr (59.0, 0.3104) | OXO-$C_9$ (88.3, 0.612) | 220, 3 | None, A + C | NA, 99.9 |
| 24, Me | 3-(4-Methyl-benzoylPr (72.3, 0.38) | OXO-$C_{13}$ (150.6, 0.75) | 205, 3 | Xylenes[c], B | 98.4, 98.0 |

NA = data not available.
[a]Pr = Propionic
[b]A = Distilled off excess alcohol only; B = distilled product; C = treated alkyl residue with charcoal.
[c]35.2 g, 0.33 moles.
[d]Ratios of alcohols given are molar ratios.

TABLE 8

| Ex. No., (R, R') | TGA 1% Wt Loss (° C.) | TGA 5% Wt Loss (° C.) | TGA 10% Wt Loss (° C.) | TGA Wt Loss, 220° C. (%) | DSC $T_g$ (° C.) | KV (20° C., mm²/sec) |
|---|---|---|---|---|---|---|
| 21, Me, $C_6$ | 136.1 | 1.67.4 | 182.8 | 42.8 | −79.1[a] | 24.15 |
| 22, Me, 2EH | 140.7 | 182.7 | 198.1 | 25.4 | −78.9[b] | 34.88 |
| 23, Me, $C_9$ | 158.5 | 191.9 | 208.0 | 16.4 | −74.2 | 45.26 |
| 24, Me, $C_{13}$ | 152.0 | 203.9 | 222.9 | 8.9 | −68.5 | 96.52 |

— = Data not taken.
2EH = 2-ethylhexyl.
[a]The DSC showed a large exotherm at −33.4° C. and a large endotherm at −1.7° C. in both the first and second heats.
[b]Potential small melting transitions, −35.1 and 50.6° C. (may represent instrument problems).

The data in Table 8 show that when a $C_{13}$ alcohol and 3-(4-methylbenzyl)propionic acid were used to synthesize the ketoester plasticizer, the viscosity and the volatility were close to those for the commercial general purpose plasticizer DINP. However, this will practically limit the use of this plasticizer platform to the $C_{13}$ alcohol derivative. Therefore, in order to design a better plasticizer structure in which other OXO-alcohols can be used. The di-methyl-substituted ($Me_2$) alkyl aromatic acids shown in Equation 5 (where R is equivalent to $R_1$ as described previously) were used to prepare related keto esters, as disclosed in Table 9 (where R is equivalent to $R_1$ as described previously), below. The volatility, viscosity, and glass transition properties of the neat plasticizers prepared in Examples 25-30 are set forth in Table 10 (where R is equivalent to $R_1$, and R' is equivalent to $R_2$, as described previously), below.

Equation 5

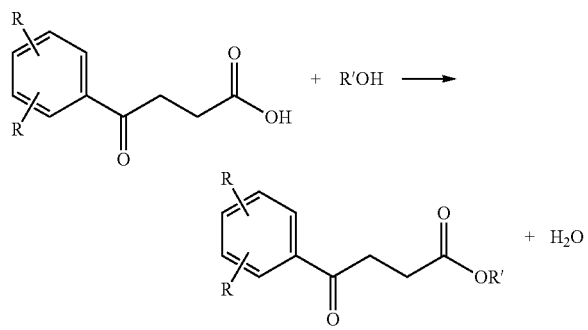

(R = $R_1$ as described previously = Me/Me or Et/H; R' = $R_2$ as described previously)

pionic acid ester plasticizers; at the same time, viscosity remains below DINP viscosity. For comparison (two methyl groups vs one ethyl group), the $C_9$ ester of the ketoacid analogous to the product of ethylbenzene acylation with succinic anhydride was prepared and evaluated. The data shows that the volatility is similar to the analogous ester which would be derived from acylation of o-xylene, but the viscosity is much lower. The viscosity of the ethyl-substituted ester is similar to the viscosity of the ester which has two methyl groups at the meta and para positions to the acyl functionality. These data indicate that a mixed acylation feed of $C_8$ alkylaromatics could be used to prepare a plasticizer, which would be much cheaper than using pure $C_8$ alkylaromatic isomers.

Further improvement on the plasticizers made using this approach was performed by using other alkyl substituents with more than 3 carbons and a methoxy substituent (equation 6, where R is equivalent to $R_1$, and R' is equivalent to $R_2$, as described previously). Data are summarized in Tables 11 and 12 (having similar equivalencies for R and R').

TABLE 9

| Ex. No., R | Carboxylic acid (grams, moles) | Alcohol (grams, moles) | Rxn Temp (° C.), Time (h) | Solvent (g, mol), Workup[a] | Acid Conv. %, Product Purity (%) |
|---|---|---|---|---|---|
| 25, $Me_2$ | 4-(2,4-dimethylphenyl)-4-OXO-butanoic (21.03, 0.102) | OXO-$C_9$ (29.5, 0.204) | 150, 11 | Xylenes (55, 0.52), A | 94.5, 98.0 |
| 26, $Me_2$ | 4-(2,4-dimethylphenyl)-4-OXO-butanoic (12.4, 0.0602) | OXO-$C_{10}$ (19.06, 0.1203) | 122, 18 | Toluene (55, 0.597), A + B | 89.0, 99.5 |
| 27, $Me_2$ | 4-(3,4-dimethylphenyl)-4-OXO-butanoic (50.4, 0.25) | OXO-$C_9$ (108.2, 0.75) | 162, 13 | Toluene (50, 0.542), A | 97.1, 98.6 |
| 28, $Me_2$ | 4-(3,5-dimethylphenyl)-4-OXO-butanoic (27.6, 0.14) | OXO-$C_9$ (58.3, 0.404) | 150, 11 | Toluene (50, 0.542), A | 97.2, 99.5 |
| 29, $Me_2$ | 4-(2,5-dimethylphenyl)-4-OXO-butanoic (47.2, 0.23) | OXO-$C_9$ (99.2, 0.69) | 175, 13 | Toluene (52.3, 0.57), A | 97.8, 99.2 |
| 30, Et | 4-(4-ethylphenyl)-4-OXO-butanoic (33.2, 0.1624) | OXO-$C_9$ (117.2, 0.812) | 170, 9 | Toluene (72.0, 0.781), C | 99.6, 99.2 |

[a] A = Washed with aqueous 3% NaOH, then water, then concentrated by distillation; B = Dried over $MgSO_4$; C = Distilled away excess alcohol and treated alkyl residue with decolorizing charcoal.

TABLE 10

| Ex. No., (R, R') | TGA 1% Wt Loss (° C.) | TGA 5% Wt Loss (° C.) | TGA 10% Wt Loss (° C.) | TGA Wt Loss, 220° C. (%) | DSC $T_g$ (° C.) | KV (20° C., $mm^2$/sec) |
|---|---|---|---|---|---|---|
| 25, 2Me, $C_9$ | 156.6 | 191.8 | 207.2 | 17.2 | −74.6 | 39.72 |
| 26, 2Me, $C_{10}$ | 169.2 | 200.6 | 215.5 | 12:2 | −74.1 | (51.33)[a] |
| 27, 2Me, $C_9$ | 165.6 | 201.8 | 217.2 | 11.2 | −69.6 | (80.55)[a] |
| 28, 2Me, $C_9$ | 161.8 | 193.8 | 209.1 | 15.8 | −73.9 | (41)[a] |
| 29, 2Me, $C_9$ | 159.1 | 192.5 | 207.6 | 17.0 | −74.0 | (44.4)[a] |
| 30, Et, $C_9$ | 166.8 | 200.2 | 215.7 | 11.9 | −78.9 | (39.1)[a] |

— = Data not taken.
[a] Cone-and-plate viscosity measurement in centiPoise (cP) taken using an Anton Paar (25 mm) viscometer (sample, size ~0.1 mL); KV not taken.

The data in Table 10 show that indeed, addition of another methyl group to the aromatic ring resulted in a decrease in the volatility using $C_9$ alcohols compared to the toluoylpro- Equation 6

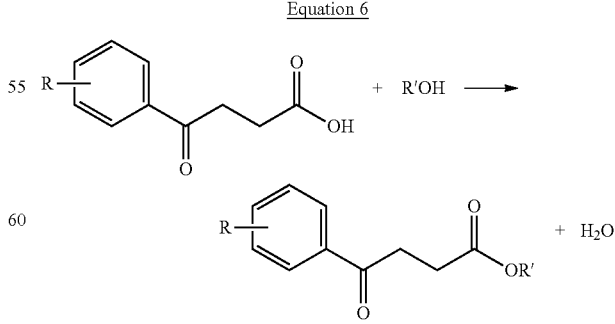

(R is equivalent to $R_1$, and R' is equivalent to $R_2$, as described previously)

TABLE 11

| Ex. No., R | Carboxylic acid (grams, moles)[a] | Alcohol (grams, moles) | Rxn Temp (° C.), Time (h) | Solvent (g, mol), Workup[b] | Acid Conv. %, Product Purity (%) |
|---|---|---|---|---|---|
| 31, t-Bu | 4-(4-t-butylphenyl)-4-OXO-butanoic (37.1, 0.1583) | OXO-$C_9$ (45.7, 0.317) | 150, 5 | Xylenes (50, 0.47), A | 95.2, 95.1 |
| 32, t-Bu | 4-(4-t-butylphenyl)-4-OXO-butanoic (12.8, 0.055) | OXO-$C_{10}$ (2.9, 0.164) | 150, 3 | Xylenes (44.63, 0.42), A | 92.3, 98.1 |
| 33, s-Bu | 4-(4-sec-butylphenyl)-4-OXO-butanoic (30.3, 0.131) | OXO-$C_9$ (56.6, 0.392) | 135, 24 | Toluene (42, 0.456), A | 98.6, 97.6 |
| 34, n-Hx | 4-(4-n-hexyl-phenyl)-4-OXO-butanoic (52.0, 0.20) | OXO-$C_9$ (87.0, 0.60) | 160, 10 | Toluene (66.7, 0.72), B | 97.8, 97.6 |
| 35, Cy | 4-(cyclo-hexylbenzyl)Pr (10.78, 0.0415) | OXO-$C_9$ (12.0, 0.0829) | 141, 16 | Xylenes (35, 0.33), A | 92.7, 94.5 |
| 35a, Cy | 4-(cyclo-hexylbenzyl)Pr (32.3, 0.124) | OXO-$C_9$ (53.9, 0.373) | 158, 7 | Xylene (73.5, 0.693), B | 89.7, 97.4 |
| 36, n-Non | 4-(4-n-nonyl-phenyl)-4-OXO-butanoic (43.2, 0.143) | OXO-$C_9$ (61.9, 0.429) | 160, 11 | Toluene (80.4, 0.87), A | 97.5, 96.5 |
| 37, O—Me | 4-(4-methoxy-benzoyl)Pr (34.6, 0.166) | OXO-$C_9$ (47.9, 0.332) | 158, 4 | Xylenes (84.8, 0.798), A | 92.4, 98.7 |

Pr = Propionic.
Cy = cyclohexyl.
[b]A = Washed with aqueous 3% NaOH, then water, then concentrated by distillation; B = Distilled away excess alcohol.

TABLE 12

| Ex. No., (R, R') | TGA 1% Wt Loss (° C.) | TGA 5% Wt Loss (° C.) | TGA 10% Wt Loss (° C.) | TGA Wt Loss, 220° C. (%) | DSC $T_g$ (° C.) | KV (20° C., mm$^2$/sec) |
|---|---|---|---|---|---|---|
| 31, t-Bu, $C_9$ | 147.0 | 206.8 | 223.7 | 8.5 | −67.4 | 130.79 |
| 32, t-Bu, $C_{10}$ | 171.8 | 209 | 225.0 | 8.0 | −65.0 | (156.6)[a] |
| 33, s-Bu, $C_9$ | 175.4 | 210.2 | 226.0 | 7.7 | −75.0 | (87.2)[a] |
| 34, n-Hx, $C_9$ | 200.1 | 232.4 | 248.2 | 2.8 | −81.8[b] | (66.1)[a] |
| 35, Cy, $C_9$ | 201.3 | 237.5 | 253.8 | 2.2 | −63.0 | (280.4)[a] |
| 35a, Cy, $C_9$ | 195.3 | 236.6 | 254.6 | 2.5 | −61.8 | (282.5)[a] |
| 36, n-Non, $C_9$ | 216.2 | 251.9 | 268.1 | 1.1 | −76.6[c] | (94.6)[a] |
| 37, OMe, $C_9$ | 173.0 | 211.4 | 226.9 | 7.3 | −69.0 | 111.45 |

— = Data not taken.
[a]Cone-and-plate viscosity measurement in centiPoise (cP); KV not taken. The 20° C. cone-and-plate viscosity for DINP = 99.2 cP compared to 96.81 mm$^2$/sec for 20° C. KV viscosity.
[b]Large exotherm, −57.0° C.; small exotherm, −36.6° C., strong melting transition, −17.5° C.; seen in both 1$^{st}$ and 2$^{nd}$ heats.
[c]Very weak; strong melting transition; −8.0° C.

The data in Table 12 show that, indeed, addition of higher carbon number (≥$C_4$) alkyl group substituents to the aromatic ring, with the use of $C_9$ alcohols, resulted in a decrease in volatility compared to analogous plasticizers with smaller substituents (all of the compounds in Table 12 show 220° C. weight losses of less than 9%, which is close to the weight loss of DINP). The viscosity remains within the target range except for the sample derived from a cyclohexylbenzene substrate.

The use of naphthalenes, alkyl naphthalenes, and partly hydrogenated (alkyl)naphthalenes (tetralins), as more stable aromatics towards acid catalysis, can also be used as a technique to improve plasticizer performance, particularly to decrease volatility without increasing the complexity of the manufacturing process through aromatic alkylation (equation 7, below).

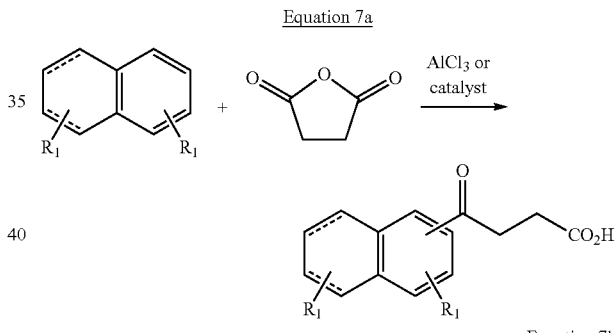

Equation 7a

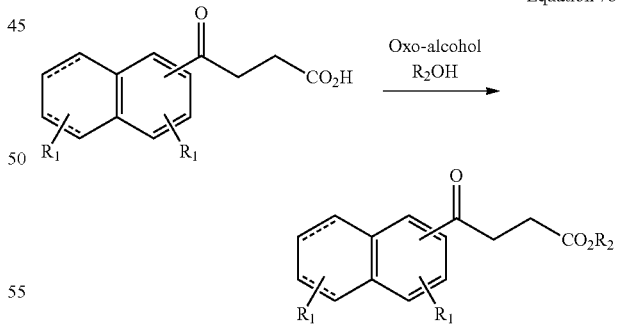

Equation 7b

Example 38A

Synthesis of 4-(1-Naphthyl)-4-oxobutanoic Acid by Acylation of Naphthalene with Succinic Anhydride 80 g (0.624 mol) of naphthalene, 20 gm (0.2 mol) of succinic anhydride, and 150 mL of nitrobenzene were placed into a 2 liter round bottom flask equipped with an addition funnel, thermometer, mechanical stirrer and nitrogen purge.

55 g (0.41 mol) of aluminum chloride dissolved into 250 mL nitrobenzene were added dropwise at 25° C. The temperature rose to 31° C. during the addition. After addition the solution was poured into a 2 liter beaker containing 100 mL HCl, 500 mL water, and 1000 mL ice. The mixture was stirred and the bottom layer was separated and placed into a round bottom flask. The flask was placed on a Kugelrohr distillation apparatus where the unreacted naphthalene and nitrobenzene were removed. The residue was dissolved into 500 mL of 5% aqueous KOH. 100 mL HCl was added to the KOH solution to precipitate the product. The product was dissolved into chloroform and dried over $MgSO_4$ then filtered. The chloroform was removed under vacuum. The residue was dissolved into hot benzene; upon cooling the product, 4-(1-naphthyl)-4-oxobutanoic acid, crystallized out (weight of crystals=14.9 g).

Example 38B

Synthesis of Oxo-$C_{10}$ Ester of 4-(1-Naphthyl)-4-oxobutanoic Acid

Into a 4-necked-250 mL round bottom flask equipped with an air stirrer, nitrogen inductor, thermometer, and chilled water cooled condenser were added 4-(1-naphthyl)-4-oxobutanoic acid (Example 38A, 16.0 g, 0.0555 mol), OXO—$C_{10}$ alcohols (26.4 g, 0.1666 mol), and xylenes (46.9 g, 0.44 mol). The reaction mixture was heated at 150-157° C. for 16 hours. The excess alcohols and xylenes were removed by vacuum distillation to 0.10 mm. The crude product was treated with charcoal (decolorizing) with magnetic stirring at room temperature for 2 hours, then filtered twice. The product remained colored with an orange color, and was found to be 95.1% pure by GC analysis. The properties of the neat ester (95.1% purity by GC) are summarized in Table 13.

Example 39A

Synthesis of 4-Oxo-4-(5,6,7,8-tetrahydronaphthalen-1-yl)butanoic Acid by Acylation of Tetralin with Succinic Anhydride In a 2 liter round bottom flask fitted with a mechanical stirrer, thermometer, condenser and nitrogen purge was added 150 gm (1.13 moles) of 1,2,3,4-tetrahydronaphthalene (tetralin). 75 gm (0.75 moles) succinic anhydride, and 750 mL benzene. A flask containing 203 gm (1.52 moles) aluminum chloride was attached to a flexible tube then attached to the reaction flask. The solid was poured, in batches, into the reaction flask over a period of 15 minutes. The temperature rose to 45° C. After addition the mixture was heated at reflux for 3 hours. The solution was cooled to room temperature then poured into a 4 liter beaker containing 2 liters of ice, 1 liter of distilled water and 200 mL of concentrated aqueous hydrochloric acid. A white precipitate formed, which was isolated by filtration. The solid was dissolved into chloroform. The chloroform solution was dried over magnesium sulfate, then filtered, and the chloroform was removed from the filtrate on a rotary evaporator. The crude residual material was dissolved into 500 mL benzene at 75° C. The solution was cooled to room temperature to crystallize the product. Product yield: 145.5 gm (0.63 moles, 86%). GC-FIMS: m/232 ($M^+$, calcd. 232.11). $^{13}C$ NMR analysis indicated a 97:3 mixture of 4-oxo-4-(5,6,7,8-tetrahydronaphthalen-1-yl)butanoic acid and 4-oxo-4-(5,6,7,8-tetrahydronaphthalen-2-yl)butanoic acid.

Example 39B

Repeat Synthesis of 4-Oxo-4-(5,6,7,8-tetrahydronaphthalen-1-yl) butanoic Acid by Acylation of Tetralin with Succinic Anhydride 100 g (0.76 mol) of tetralin, 50 g (0.2 mol) of succinic anhydride, and 500 mL of benzene were placed into a 1 liter round bottom flask equipped with an addition funnel, thermometer, mechanical stirrer and nitrogen purge. A flask containing 134 g (1.0 mol) of aluminum chloride was attached to the reaction flask using a flexible tube. The solid was slowly added to the flask at 25° C. over a period of ten minutes. The temperature rose to 40° C. during addition. After addition the solution was heated and refluxed for 3 hours. The solution was cooled, then poured into a 2 liter beaker containing 100 mL aqueous HCl, 500 mL water, and 1000 mL ice. A white precipitate formed, which was collected by filtration. The white solid was dissolved into chloroform and dried over $MgSO_4$, then filtered. The chloroform was removed from the filtrate under vacuum. The residue was dissolved into 200 mL hot benzene, upon cooling, the product, 4-oxo-4-(5,6,7,8-tetrahydronaphthalen-1-yl)butanoic acid, crystallized out (weight of crystals=64.8 g). $^{13}C$ NMR analysis indicated a similar isomer distribution to Example 39A (97:3).

Example 39C

Synthesis of Oxo-$C_{10}$ Ester of 4-Oxo-4-(5,6,7,8-tetrahydronaphthalen-1-yl)butanoic Acid Into a 4-necked-1000 mL round bottom flask equipped with an air stirrer, nitrogen inductor, thermometer, and chilled water cooled condenser were added 4-(5,6,7,8-tetrahydronaphthyl)-4-oxobutanoic acid (Examples 39A/B, 122.6 g, 0.5278 mol), OXO—$C_{1-10}$ alcohols (297.2 g, 1.88 mol), and toluene (106.2 g, 1.153 mol). The reaction mixture was heated at 150-159° C. for 14 hours. The excess alcohols and toluene were removed by vacuum distillation to 0.10 mm. The crude product was treated with charcoal (decolorizing) with magnetic stirring at room temperature for 2 hours, then filtered twice. The product remained yellow and was found to be 97.9% pure by GC analysis. The properties of the neat ester, assumed to contain 3% of the 2-yl isomer (97.97% purity by GC), are summarized in Table 13.

TABLE 13

| Ex. No., Structure | TGA 1% Wt Loss (° C.) | TGA 5% Wt Loss (° C.) | TGA 10% Wt Loss (° C.) | TGA Wt Loss, 220° C. (%) | DSC $T_g$ (° C.) | Viscosity (20° C., cP)$^a$ |
|---|---|---|---|---|---|---|
| 38B, $C_{10}$ ester of 4-(1-naphthyl)-4-oxobutanoic acid | 188.1 | 233.5 | 252.2 | 2.9 | −62.6 | 248.95 |

TABLE 13-continued

| Ex. No., Structure | TGA 1% Wt Loss (° C.) | TGA 5% Wt Loss (° C.) | TGA 10% Wt Loss (° C.) | TGA Wt Loss, 220° C. (%) | DSC $T_g$ (° C.) | Viscosity (20° C., cP)[a] |
|---|---|---|---|---|---|---|
| 39C, C10 ester of 4-oxo-4-(5,6,7,8-tetrahydronaphthalen-1-yl)butanoic acid w/3% of 2-yl isomer (97.95%) | 191.7 | 229.4 | 246.2 | 3.3 | −63.7 | 80.55 |

[a]Cone-and-plate (Anton Paar) viscosity.

The data in Table 13 show that, indeed, use of naphthalene- or tetrahydronaphthalene-based aromatics provides plasticizers with excellent volatility, even without the necessity of appending alkyl substituents from the ring(s). Increases in viscosity seen for naphthalene-based esters can be corrected by use of a more flexible tetrahydronaphthalene (tetralin) substrate.

Table 14 shows the calculated solubility parameters of the esters prepared in Examples 38B and 39C versus diisononyl phthalate (DINP). The data show that the esters have similar solubility parameters to DINP.

TABLE 14

| Plasticizer | Solubility Parameter |
|---|---|
| DINP | 8.767578947 |
| 38B, $C_{10}$ ester of 4-(1-naphthyl)-4-oxobutanoic acid | 8.656306849 |
| 39C, $C_{10}$ ester of 4-oxo-4-(5,6,7,8-H$_4$-naphthalen-1-yl)butanoic acid | 8.804591304 |

Example 40

Hydrolytic Stability Comparison Between OXO—$C_9$ Benzoylbenzoate and Benzoylpropionate Esters and DINP A 120 mL glass Parr reactor was charged with 25 grams of a 0.05N HCl solution plus 75 grams of either the OXO—$C_9$ benzoylbenzoate ester prepared in Example 3, the OXO—$C_9$ benzoylpropionate ester prepared in Example 18, or the commercial plasticizer DINP (diisononyl phthalate). The mixture was stirred for 33 days at 91-104° C. with GC sampling throughout the heating period to quantify the amount of triglyceride hydrolyzed to diglyceride or other byproducts ("% TG conversion"). Data are shown in FIG. 1.

Example 41

General Procedure for Plasticization of Poly(Vinyl Chloride) and Properties of Plasticized PVC Bars A 5.85 g portion of the desired ester (or comparative commercial plasticizer DINP) was weighed into an Erlenmeyer flask which had previously been rinsed with uninhibited tetrahydrofuran (THF) to remove dust. An 0.82 g portion of a 70:30 by weight solid mixture of powdered Drapex® 6.8 (Crompton Corp.) and Mark® 4716 (Chemtura USA Corp.) stabilizers was added along with a stirbar. The solids were dissolved in 117 mL uninhibited THF. Oxy Vinyls® 240F PVC (11.7 g) was added in powdered form and the contents of the flask were stirred overnight at room temperature until dissolution of the PVC was complete (a PVC solution for preparation of an unplasticized comparative sample was prepared using an identical amount of stabilizer, 100 mL solvent, and 13.5 g PVC). The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a 5 min period. The resultant clear film was carefully peeled off of the aluminum, flipped over, and placed back evenly into the pan. The pan was then placed in a vacuum oven at 70° C. overnight to remove residual THF. The dry, flexible film was carefully peeled away and exhibited no oiliness or inhomogeneity unless otherwise noted. The film was cut into small pieces to be used for preparation of test bars by compression molding (size of pieces was similar to the hole dimensions of the mold plate). The film pieces were stacked into the holes of a multi-hole steel mold plate, pre-heated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon®-coated aluminum foil and the following multistage press procedure was used at 170° C. with no release between stages: (1) 3 minutes with 1-2 tons overpressure; (2) 1 minute at 10 tons; (3) 1 minute at 15 tons; (4) 3 minutes at 30 tons; (5) release and 3 minutes in the cooling stage of the press (7° C.) at 30 tons. A knockout tool was then used to remove the sample bars with minimal flexion. Typically, flexible bars were obtained which, when stored at room temperature, showed no oiliness or exudation several weeks after pressing unless otherwise noted.

Two each of the sample bars were visually evaluated for appearance and clarity and further compared to identically prepared bars plasticized with DINP by placing the bars over a standard printed text initially and at the end of the test (typically around Day 21). The qualitative and relative flexibility of the bars was also evaluated by hand. The various bars were evaluated in different test batches; thus, a new DINP control bar was included with each batch. The DINP bars were colorless. The bars were placed in aluminum pans which were then placed inside a glass crystallization dish covered with a watch glass. The bars were allowed to sit under ambient conditions at room temperature for at least three weeks and re-evaluated during and/or at the end of this aging period. Table 15 (where R is equivalent to $R_1$, and R' is equivalent to $R_2$, as described previously) presents appearance rankings and notes. The colors of the bars generally reflected the colors of the neat plasticizers.

TABLE 15

| Example No. of Plasticizer Used in Bar (A, R, R')[a] | Initial Clarity (Day)[b] | Final Clarity (Day) | Notes on Bar at End of Test |
|---|---|---|---|
| 1 (Bz, H, C$_6$) | — | 1 (26) | Somewhat stiff ~ DINP |
| 2 (Bz, H, 2EH) | 1 (0) | 1 (38) | V lt yellow, mod. stiff, < DINP |
| 3 (Bz, H, C$_9$) | 1 (14) | — | Sl. stiff., sl. > DINP |
| 4 (Bz, H, n-C$_9$) | 1 (0) | 1 (38) | OK flex, sl. > DINP |
| 5 (Bz, Me, C$_5$) | — | 1 (26) | Quite stiff < DINP |
| 6 (Bz, Me, C$_6$) | — | 1 (26) | Quite stiff < DINP |
| 7 (Bz, Me, 2EH) | 1 (0) | 1 (38) | V. lt. orange, quite stiff < DINP |
| 8 (Bz, Me, C$_9$) | — | 1 (26) | Quite stiff < DINP |
| 17 (Pr, H, 2EH) | 1 (0) | 1 (38) | Lt. yellow, excellent flex > DINP |
| 18 (Pr, H, C$_9$) | 1 (14) | — | Excell. flex, > DINP; yellow |
| 19 (Pr, H, C$_{13}$) | 1 (14) | — | Good flex, > DINP; yellow |
| 20 (Pr, H, n-C$_9$) | 1 (0) | 1 (38) | Yellow, excellent flex |
| 21 (Pr, Me, C$_6$) | — | 1 (26) | Extremely flexible |
| 22 (Pr, Me, 2EH) | 1 (0) | 1 (38) | Yellow, excellent flex > DINP |
| 23 (Pr, Me, C$_9$) | — | 1 (26) | Very flexible |
| 24 (Pr, Me, C$_{13}$) | — | 1 (26) | Good flex |
| 25 (Pr, op-2Me, C$_9$) | 1 (0) | 1.5 (38) | Yellow, v. good flex > DINP |
| 26, (Pr, op-2Me, C$_{10}$) | 2 (13) | 2 (23) | Yellow, hazy, mod. good flex > DINP |
| 27 (Pr, mp-2Me, C$_9$) | — | 1 (21) | V lt. yellow, good/v. good flex |
| 28 (Pr, mm-2Me, C$_9$) | — | 1.5 (21) | V. lt. yellow, sl. hazy, good/v. good flex |
| 29 (Pr, om-2Me, C$_9$) | — | 1 (21) | Lt. yellow, good/v. good flex |
| 30 (Pr, Et, C$_9$) | 1 (7) | 1 (39) | Yellow, very good flex (Day 7) |
| 31 (Pr, t-Bu, C$_9$) | 1 (13) | 1 (23) | Yellow, mod. stiff < DINP |
| 32 (Pr, t-Bu, C$_{10}$) | — | 2 (21) | Hazy, med/dark orange, sl. stiff |
| 33 (Pr, s-Bu, C$_9$) | 1 (9) | 1 (27) | Yellow, Ok flex/sl. stiff, sl. < DINP |
| 34 (Pr, n-Hx, C$_9$) | 1 (7) | 1 (39) | Orange, OK flex > DINP (Day 39) |
| 35 (Pr, Cy, C$_9$) | 2.5 (13) | 2.5 (23) | Yellow, hazy, somewhat stiff |
| 35a (Pr, Cy, C$_9$) | 1 (7) | 1 (39) | Yellow, mod. stiff, sl. < DINP (Day 7) |
| 36 (Pr, n-Non, C$_9$) | 1 (7) | 1.5 (39) | Dark orange, stiff, flex ~DINP (Day 39) |
| 37 (Pr, OMe, C$_9$) | 2 (13) | 2 (23) | Yellow, hazy, good flex |
| 38B (Naphthyl Pr, C$_{10}$) | 1 (13) | 1 (41) | Dark red, Ok/good flex (>DINP) |
| 39C (H$_4$-Naphthyl Pr, C$_{10}$) | 1 (4) | 1 (35) | Lt. orange, sl. stiff (sl. <DINP) |
| DINP ctrl A[c] | 1 (14) | — | somewhat stiff |
| DINP ctrl B[c] | — | 1 (26) | Somewhat stiff |
| DINP ctrl C[c] | 1 (0) | 1 (38) | Lt orange, OK flex/minorly stiff |
| DINP ctrl D[c] | 1 (13) | 1 (23) | Somewhat stiff |
| DINP ctrl E[c] | — | 1 (21) | OK flex/sl. stiff |
| DINP ctrl F[c] | 1 (9) | 1 (27) | OK flex |
| DINP ctrl G[c] | 1 (7) | 1 (39) | OK flex/sl. Stiff |
| DINP ctrl H[c] | 1 (13) | 1 (41) | OK flex/sl. stiff |
| DINP ctrl I[c] | 1 (4) | 1 (35) | OK flex/sl. stiff |

— Data not taken.
[a] "A" commonly denotes the parent structure of the keto-acid chain spacer; Bz = benzoate; Pr = propionate.
[b] 1-5 scale, 1 = no distortion, 5 = completely opaque; "Day" denotes days after pressing that the bar was evaluated; Day 0 = day of pressing.
[c] A = Ex. 3, 18, 19 test batch; B = Ex. 1, 5, 6, 8, 21, 23, 24 test batch; C = Ex. 2, 4, 7, 17, 20, 22, 25 test batch; D = Ex. 26, 31, 35, 37 test batch; E = 27, 28, 29, 32 test batch; F = Ex. 33 test batch; G = Ex. 30, 34, 35a, 36 test batch; H = Ex. 38B test batch; I = Ex. 39C test batch.

Example 42

98° C. Weight Loss Study of Plasticized PVC Bars

Two each of the PVC sample bars prepared in Example 41 were placed separately in aluminum weighing pans and placed inside a convection oven at 98° C. Initial weight measurements of the hot bars and measurements taken at specified time intervals were recorded and results were averaged between the bars. The averaged results are shown in Table 16 (with R and R' definitions as given in Table 15). Notes on the appearance and flexibility of the bars at the end of the test are also given. The final color of the bars (even DINP control samples) varied between batches; gross comparisons only should be made between bars of different test batches.

TABLE 16

| Ex. No. of Plasticizer Used in Bar (A, R, R')[a] | Day 1 | Day 2 | Day 3 | Day 7 | Day 14 | Day 21 | Notes on Bar at End of Test |
|---|---|---|---|---|---|---|---|
| 1 (Bz, H, C$_6$) | 0.2 | 0.45 | 0.75[d] | 0.99 | 2.19 | 3.21 | Med orange, stiff |
| 2 (Bz, H, 2EH) | 0.18 | 0.18 | — | 0.89 | 1.11 | 1.25[f] | Orange, quite stiff < DINP[f] |
| 3 (Bz, H, C$_9$) | 0.40 | 0.46 | 0.81[b] | 0.79 | 1.37 | 1.79 | Lt brown, somewhat stiff |
| 4 (Bz, H, n-C9) | 0.06 | 0.14 | — | 0.35 | 0.38 | 0.58[j] | Lt orange, OK flex < DINP, sl. stiff[j] |

TABLE 16-continued

| Ex. No. of Plasticizer Used in Bar (A, R, R')[a] | Day 1 | Day 2 | Day 3 | Day 7 | Day 14 | Day 21 | Notes on Bar at End of Test |
|---|---|---|---|---|---|---|---|
| 5 (Bz, Me, $C_5$) | 0.43 | 0.51 | 0.77[d] | 1.07 | 1.57 | 2.29 | Med-lt orange, stiff |
| 6 (Bz, Me, $C_6$) | 0.32 | 0.29 | 0.68[d] | 0.80 | 1.27 | 1.77 | Med orange, stiff |
| 7 (Bz, Me, 2EH) | 0.20 | 0.30 | — | 0.36 | 0.69 | 1.14[h] | Med lt orange, quite stiff < DINP[h] |
| 8 (Bz, Me, $C_9$) | 0.23 | 0.23 | 0.20[d] | 0.28 | 0.51 | 0.54 | Lt yellow, somewhat stiff, sl. < DINP |
| 17 (Pr, H, 2EH) | 0.49 | 0.66 | — | 3.50 | 6.10 | 7.12 | Lt orange, v stiff, curled[g] |
| 18 (Pr, H, $C_9$) | 0.24 | 0.30 | 0.70[b] | 0.71 | 1.35 | 1.79 | Good flex > DINP, yellow |
| 19 (Pr, H, $C_{13}$) | 0.21 | 0.17 | 0.36[b] | 0.34 | 0.49 | 0.53 | Good flex > DINP, yellow |
| 20 (Pr, H, n-$C_9$) | 0.12 | 0.30 | — | 0.84 | 1.07 | 1.83[k] | Lt yellow, v good flex~DINP[k] |
| 21 (Pr, Me, $C_6$) | 0.57 | 1.03 | 3.74 | 4.13 | 6.23 | 8.34 | Lt yellow, somewhat stiff, sl. < DINP, sl. curled |
| 22 (Pr, Me, 2EH) | 0.43 | 0.56 | — | 0.65 | 1.40 | 3.28[i] | Lt yellow, v good flex~DINP[i] |
| 23 (Pr, Me, $C_9$) | 0.26 | 0.34 | 0.64[d] | 0.90 | 1.61 | 2.58 | Med yellow, good flex > DINP, curled |
| 24 (Pr, Me, $C_{13}$) | 0.19 | 0.24 | 0.37[d] | 0.35 | 0.47 | 0.52 | Med yellow, excel. flex > DINP., sl. curled |
| 25 (Pr, op-2Me, $C_9$) | 0.24 | 0.38 | — | 0.57 | 1.60 | 2.07[j] | Yellow, v good flex~DINP[j] |
| 26, (Pr, op-2Me, $C_{10}$) | 0.20 | — | 0.71[d] | 0.78 | 0.84 | 1.16 | Yellow, hazy, curled, v good flex |
| 27 (Pr, mp-2Me, $C_9$) | — | — | 0.48[e] | 0.61 | 0.86 | 1.20 | Lt orange, curled, excellent flex |
| 28 (Pr, mm-2Me, $C_9$) | — | — | 0.71[e] | 0.87 | 1.51 | 2.13 | Lt yellow, sl. hazy, OK/good flex |
| 29 (Pr, om-2Me, $C_9$) | — | — | 0.98[e] | 1.32 | 1.78 | 2.75 | Lt yellow, curled, excellent flex |

Example 43

70° C. Humid Aging Study of Plasticized PVC Bars

Using a standard one-hole office paper hole punch, holes were punched in two each of the sample bars prepared in Example 41 ⅛" from one end of the bar. The bars were hung in a glass pint jar (2 bars per jar) fitted with a copper insert providing a stand and hook. The jar was filled with ½" of distilled water and the copper insert was adjusted so that the bottom of each bar was 1" above the water level. The jar was sealed, placed in a 70° C. convection oven, and further sealed by winding Teflon® tape around the edge of the lid. After 21 days the jars were removed from the oven, allowed to cool for 20 minutes, opened, and the removed bars were allowed to sit under ambient conditions in aluminum pans (with the bars propped at an angle to allow air flow on both faces) or hanging from the copper inserts for 1 week (until reversible humidity-induced opacity had disappeared). The bars were evaluated visually for clarity. All bars exhibited complete opacity during the duration of the test and for several days after removal from the oven. Results are shown in Table 17 (with R and R' definitions as given in Table 15). Notes on the appearance and flexibility of the bars at the end of the test are also given.

TABLE 17

| Example No. of Plasticizer Used in Bar (A, R, R')[a] | Clarity (Days Ambient Aging) | Notes on Bar at End of Test |
|---|---|---|
| 1 (Bz, H, $C_6$) | 1 (20) | OK flex |
| 2 (Bz, H, 2EH) | 3 (28) | Oily, sticky, hazy, mod. stiff, white spots |
| 3 (Bz, H, $C_9$) | 1 (14) | Somewhat stiff < DINP, some opaque spots |
| 4 (Bz, H, n-$C_9$) | 2.5 (28) | OK flex/sl.stiff, many white spots, oily, sticky |
| 5 (Bz, Me, $C_5$) | 1.5 (20) | Stiff |
| 6 (Bz, Me, $C_6$) | 1.5 (20) | Fairly stiff, maybe sl. sticky |
| 7 (Bz, Me, 2EH) | 1 (28) | Somewhat stiff, few white spots |
| 8 (Bz, Me, $C_9$) | 1 (20) | Fairly stiff |
| 17 (Pr, H, 2EH) | 1 (28) | Excellent flex, few white spots |

TABLE 17-continued

| Example No. of Plasticizer Used in Bar (A, R, R')[a] | Clarity (Days Ambient Aging) | Notes on Bar at End of Test |
|---|---|---|
| 18 (Pr, H, $C_9$) | 1 (14) | Extr. good flex, >>DINP |
| 19 (Pr, H, $C_{13}$) | 1 (14) | Good flex > DINP |
| 20 (Pr, H, n-$C_9$) | 1 (28) | Excellent flex |
| 21 (Pr, Me, $C_6$) | 1 (20) | Excellent flex, quick return to clarity |
| 22 (Pr, Me, 2EH) | 1 (28) | Excellent flex |
| 23 (Pr, Me, $C_9$) | 1 (20) | Excellent flex, quick return to clarity |
| 24 (Pr, Me, $C_{13}$) | 1 (20) | V good flex, quick return to clarity |
| 25 (Pr, op-2Me, $C_9$) | 1.5 (28) | V good flex, curled |
| 26, (Pr, op-2Me, $C_{10}$) | 1.5 (29) | OK flex/slightly stiff |
| 27 (Pr, mp-2Me, $C_9$) | 1 (18) | Excellent flex, white spots, minor oil |
| 28 (Pr, mm-2Me, $C_9$) | 1.5 (18) | Excellent flex, oily, many white spots |
| 29 (Pr, om-2Me, C9) | 1 (18) | Excellent flex, very minor white spots/oil |
| 30 (Pr, Et, $C_9$) | 1 (18) | Excellent flex, minor white spots/oil |
| 31 (Pr, t-Bu, $C_9$) | 1.5 (29) | Good flex |
| 32 (Pr, t-Bu, $C_{10}$) | 2 (18) | Orange, somewhat stiff, sl. < DINP |
| 33 (Pr, s-Bu, $C_9$) | 2 (30) | Excellent flex, oily, hazy |
| 34 (Pr, n-Hx, $C_9$) | 1 (18) | Good flex, no oil |
| 35 (Pr, Cy, $C_9$) | 3.5 (29) | Stiff |
| 35a (Pr, Cy, $C_9$) | 1 (18) | Sl./mod. stiff (< DINP), minor white spots/oil |
| 36 (Pr, n-Non, $C_9$) | 5 (18) | Stiff, v. sl. fingerprints, no oil |
| 37 (Pr, OMe, $C_9$) | 1.5 (29) | Very good flex |
| 38B (Naphthyl Pr, $C_{10}$) | 1 (20) | Good flex |
| 39C ($H_4$-Naphthyl Pr, $C_{10}$) | 1 (14) | Very good flex |
| DINP ctrl A[c] | 1 (14) | Slightly stiff |
| DINP ctrl B[c] | 1.5 (20) | OK/good flex |
| DINP ctrl C[c] | 1 (28) | Good flex |
| DINP ctrl D[c] | 1 (29) | OK flex/somewhat stiff |
| DINP ctrl E[c] | 1 (18) | V lt yellow, v minor white spots, OK flex/sl. stiff |
| DINP ctrl F[c] | 1 (30) | OK flex, very minor oil, white spots, haze |
| DINP ctrl G[c] | — | — |
| DINP ctrl H[c] | 1 (20) | OK flex/sl stiff |
| DINP ctrl I[c] | 1 (14) | Very good flex |

— Data not taken.
[a]"A" commonly denotes the parent structure of the keto-acid chain spacer; Bz = benzoate; Pr = propionate.
[b]1-5 scale, 1 = no distortion, 5 = completely opaque.
[c]See Table 15.

Example 44

Weight Loss Study of Plasticized PVC Bars

A small portion of the plasticized sample bars prepared in Example 41, or alternately a small piece of thin material taken from the mold overflow, were subjected to Thermogravimetric Analysis as previously described to evaluate plasticizer volatility in the formulated test bars for selected samples. Results are shown in Table 18 (with A, R, and R' as defined earlier and in Table 15).

TABLE 18

% Weight Loss by TGA of Plasticized PVC Bars.

| Ex. No. of Material Used in Bar (A, R, R') | TGA 1% Loss (° C.) | TGA 5% Loss (° C.) | TGA 10% Loss (° C.) | % Loss, 220° C. |
|---|---|---|---|---|
| DINP | 204.6 | 247.4 | 257.6 | 1.8[a] |
| 3 (Bz, H, $C_9$)[c] | 203.6 | 240.5 | 251.2 | 2.0[a,b] |
| 3 (Bz, H, $C_9$), repeat[d] | 195.1 | 237.7 | 248.3 | 2.6[a] |
| 18 (Pr, H, $C_9$)[e] | 173.2 | 210.6 | 233.9 | 6.9[b] |
| 18 (Pr, H, $C_9$), repeat[f] | 169.8 | 206.7 | 229.7 | 7.8[a] |
| 26 (Pr, op-2Me, $C_{10}$)[g] | 187.6 | 228.9 | 246.3 | 3.7[b] |
| 26 (Pr, op-2Me, $C_{10}$), rpt[h] | 181.2 | 225.8 | 248.1 | 4.2[a] |
| 31 (Pr, t-Bu, $C_9$)[i] | 190.7 | 235.1 | 248.8 | 2.7[a] |
| 31 (Pr, t-Bu, $C_9$), repeat[j] | 196.8 | 236.1 | 248.8 | 2.7[a] |
| 37 (Pr, OMe, $C_9$)[k] | 189.1 | 229.5 | 247.0 | 3.3[a], 4.7[b] |
| 37 (Pr, OMe, $C_9$), repeat[l] | 200.4 | 238.5 | 248.7 | 2.3[a] |

[a]Bar.
[b]Circle of thin film (mold overflow).
[c]Bar/film aged 397/392 days.
[d]Re-pressed bar aged 8 days.
[e]Film aged 392 days.
[f]Re-pressed bar aged 9 days.
[g]Film aged 225 days.
[h]Re-pressed bar aged 7 days, made using scaled up material as described in Ex. 46.
[i]Film aged 224 days.
[j]Re-pressed bar aged 9 days.
[k]Bar/film aged 229/225 days.
[l]Re-pressed bar aged 9 days.

Example 45

Demonstration of PVC Plasticization by Differential Scanning Calorimetry (DSC) and Dynamic Thermal Mechanical Analysis (DMTA)

Three-point bend Dynamic Mechanical Thermal Analysis (DMTA) with a TA Instruments DMA Q980 fitted with a liquid $N_2$ cooling accessory and a three-point bend clamp assembly was used to measure the thermo-mechanical performance of neat PVC and the PVC/plasticizer blend sample bars prepared in Example 41. Samples were loaded at room temperature and cooled to −60° C. or lower at a cooling rate of 3° C./min. After equilibration, a dynamic experiment was performed at one frequency using the following conditions: 3° C./min heating rate, 1 Hz frequency, 20 micrometer amplitude, 0.01 pre-load force, force track 120%. Two or three bars of each sample were typically analyzed; numerical data was taken from the bar typically exhibiting the highest room temperature storage modulus (the bar assumed to have the fewest defects) unless another run was preferred for data quality. Glass transition onset values were obtained by extrapolation of the tan delta curve from the first deviation from linearity. The DMTA measurement gives storage modulus (elastic response modulus) and loss modulus (viscous response modulus); the ratio of loss to storage moduli at a given temperature is tan delta. The beginning (onset) of the $T_g$ (temperature of brittle-ductile transition) was obtained for each sample by extrapolating a tangent from the steep inflection of the tan delta curve and the first deviation of linearity from the baseline prior to the beginning of the peak. Table 19 provides a number of DMTA parameters for the bars (the temperature at which the storage modulus equals 100 MPa was chosen to provide an arbitrary measure of the temperature at which the PVC loses a set amount of rigidity; too much loss of rigidity may lead to processing complications for the PVC material). The flexible use temperature range of the samples was evaluated as the range between the $T_g$ onset and the temperature at which the storage modulus was 100 MPa. A lowering and broadening of the glass transition for neat PVC was observed upon addition of the OXO ester plasticizers, indicating plasticization. Plasticization (enhanced flexibility) was also demonstrated by lowering of the PVC room temperature storage modulus. Differential Scanning Calorimetry (DSC) was also performed on the compression-molded sample bars (−90° C. to 100-170° C. at 10° C./min). Small portions of the sample bars (~5-7 mg) were cut for analysis, making only vertical cuts perpendicular to the largest surface of the bar to preserve the upper and lower compression molding "skins"; the pieces were then placed in the DSC pans so that the upper and lower "skin" surfaces contacted the bottom and top of the pan. Alternately, pieces of leftover thin film were used. Results are summarized in Table 19 (with A, R, and R' as defined earlier and in Table 15); lowering and broadening of the glass transition for neat PVC indicates plasticization by the OXO-esters (for aid in calculating the numerical values of these broad transitions, the DSC curve for each plasticized bar was overlaid with the analogous DMTA curve for guidance about the proper temperature regions for the onset, midpoint, and end of $T_g$).

TABLE 19

DMTA and DSC Thermal Parameters for Plasticized PVC Bars

| Ex. No. of Material Used in Bar (A, R, R') | Tan Δ $T_g$ Onset (° C.) | Tan Δ Pk (° C.) | 25° C. St. Mod. (MPa) | Temp. of 100 MPa St. Mod. (° C.) | Flex. Use Rge (° C.)[a] | DSC $T_g$ Onset (° C.) | DSC $T_g$ Midpt (° C.) | DSC $T_g$ End (° C.) | $T_m$ Max (° C.), ΔH$_f$ (J/g)[b] |
|---|---|---|---|---|---|---|---|---|---|
| DINP | −37.6 | 17.1 | 48.6 | 16.9 | 54.5 | −37.8 | −24.8 | −12.2 | N/A[d] |
| 3 (Bz, H, C$_9$)[c] | — | — | — | — | — | −13.9 | −0.3 | 13.4 | 60.9, N/A[e] |
| 3 (Bz, H, C$_9$), rpt[f] | −18.5 | 23.6 | 42.6 | 18.8 | 37.3 | −15.8 | −0.3 | 15.4 | 56.1, 0.56 |
| 18 (Pr, H, C$_9$)[g] | — | — | — | — | — | −50.1 | −34.9 | −19.9 | 64.2, N/A |
| 18 (Pr, H, C$_9$), rpt[h] | −41.8 | 5.9 | 12.2 | 4.3 | 46.1 | −42.4 | −19.0 | 4.3 | 55.9, 0.86 |
| 26 (Pr, op-2Me, C$_{10}$)[i] | — | — | — | — | — | −48.8 | −30.0 | −11.1 | 62.9, 1.43 |
| 26 (Pr, op-2Me, C$_{10}$), rpt[j] | −45.4 | 23.5 | 85.5 | 23.6 | 69.0 | −29.0 | −7.2 | 14.6 | 54.3, 1.06 |
| 31 (Pr, t-Bu, C$_9$)[k] | — | — | — | — | — | −39.5 | −25.9 | −12.5 | 61.2, 1.28 |
| 31 (Pr, t-Bu, C$_9$), rpt[l] | −24.5 | 32.8 | 117.5 | 26.4 | 50.9 | −31.0 | −10.6 | 9.8 | 55.9, 0.79 |
| 37 (Pr, OMe, C$_9$)[m] | — | — | — | — | — | −30.6 | −12.8 | 5.0 | 62.2, 2.03 |
| 37 (Pr, OMe, C$_9$), rpt[n] | −37.2 | 9.1 | 17.4 | 8.1 | 45.3 | −40.4 | −21.3 | −2.2 | 56.1, 0.57 |
| None[c] | 44.0 | 61.1 | 1433 | 57.1 | 13.1 | 44.5 | 46.4 | 48.9 | N/A |

N/A = Not analyzed.
[a]Difference between DMTA temperature of 100 MPa storage modulus and onset of $T_g$.
[b]Some sample bars showed a weak melting point ($T_m$) from the crystalline portion of PVC. Often this weak transition was not specifically analyzed, but data is given here in instances where it was recorded.
[c]Neat PVC, no plasticizer used.
[d]Very small.
[e]Bar, aged 399 days; 2$^{nd}$ small endotherm peak at 93.7° C.
[f]Remade bar (DMTA) and film (DSC), aged 20/9 (DMTA/DSC) days.
[g]Bar, aged 399 days; 2$^{nd}$ small endotherm peak at 89.9° C.
[h]Remade bar (DMTA) and film (DSC), aged 15/9 (DMTA/DSC) days.
[i]Bar, aged 232 days.
[j]Remade bar (DMTA) and film (DSC), aged 8/7 (DMTA/DSC) days.
[k]Bar, aged 231 days. 2$^{nd}$ small endotherm peak at 87.4.
[l]Remade bar (DMTA) and film (DSC), aged 15/9 (DMTA/DSC) days.
[m]Bar, aged 231 days.
[n]Remade bar (DMTA) and film (DSC), aged 17/9 (DMTA/DSC) days.

Example 46

Further Demonstration of PVC Plasticization with Benzoyl Propionate OXO-Esters Plasticized PVC samples containing the substituted benzoyl propionate OXO-esters of Examples 26, 31, and 37 (prepared similarly, but on larger scale) or DINP (as a comparative) were mixed at room temperature with moderate stirring, then placed on a roll mill at 340° F. and milled for 6 minutes. The flexible vinyl sheet was removed and compression molded at 340° F. The samples had the following formulation: 100 phr Oxy Vinyls® 240 PVC resin; 50 phr OXO-ester or DINP; 3 phr epoxidized soybean oil; 2.5 phr Mark® 1221 Ca/Zn stabilizer; 0.25 phr stearic acid. Comparison of the data for the formulations is given in Table 20 (with A, R, and R' as defined earlier and in Table 15). A ⅜" Loop Test showed no changes (acceptable) for all samples. In a 100% Relative Humidity Test (70° C., 11 days), the samples containing DINP and the Ex. 37 (OMe) plasticizer showed a moderate change from original; each sample was sticky and had an opaque appearance. The sample containing the Ex. 31 (t-Bu) plasticizer showed a slight change having some stickiness, but less opacity. The sample containing the Ex. 36 (op-2Me) plasticizer had almost no stickiness and minor changes in appearance.

The OXO-ester plasticizers of the present application find use in a number of different polymers, such as vinyl chloride resins, polyesters, polyurethanes, ethylene-vinyl acetate copolymers, rubbers, poly(meth)acrylics and mixtures thereof.

Claims for PCT Filing:

1. A process for making non-phthalate plasticizers, comprising acylating an aromatic compound with a succinic anhydride to form a keto-acid, and esterifying the keto-acid with $C_4$-$C_{13}$ OXO-alcohols to form a plasticizer compound.

2. The process of claim 1, wherein the aromatic compound is of the formula:

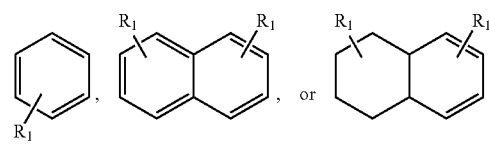

wherein $R_1$ is selected from the group consisting of H, $C_1$-$C_9$ linear or branched alkyl, cycloalkyl, or $C_1$-$C_4$ ether and wherein there may be 1 or 2 $R_1$ groups present on the

TABLE 20

Properties of PVC Samples Plasticized With 50 phr Benzoyl Propionate OXO-Esters Versus DINP

| Plasticizer Used in Formulation (A, R, R') | Ex. 26 (Pr, op-2Me, $C_{10}$) | Ex. 31 (Pr, t-Bu, $C_9$) | Ex. 37 (Pr, OMe, $C_9$) | DINP |
|---|---|---|---|---|
| Original Mechanical Properties | | | | |
| Shore A Hardness (15 sec.) | 77.5 | 80.6 | 75.7 | 80.3 |
| 95% Confidence Interval | 1.1 | 0.2 | 1.3 | 0.8 |
| Shore D Hardness (15 sec.) | 22.7 | 23.2 | 20.1 | 22.7 |
| 95% Confidence Interval | 0.3 | 0.4 | 0.4 | 0.4 |
| 100% Modulus Strength, psi | 1648 | 1846 | 1575 | 1691 |
| 95% Confidence Interval | 25 | 17 | 25 | 13 |
| Ultimate Tensile Strength, psi | 3263 | 3316 | 3287 | 3267 |
| 95% Confidence Interval | 62 | 158 | 66 | 48 |
| Ultimate Elongation, % | 341 | 342 | 338 | 367 |
| 95% Confidence Interval | 11 | 21 | 9 | 17 |
| Aged Mechanical Properties (7 days at 100° C., AC/hour) | | | | |
| Aged 100% Modulus Strength, psi | N/A* | 2299 | 2677 | 2390 |
| 95% Confidence Interval | N/A* | 879 | 54 | 31 |
| Ultimate Tensile Strength, psi | 3812 | 3303 | 3531 | 3013 |
| 95% Confidence Interval | 1369 | 205 | 40 | 57 |
| Ultimate Elongation, % | 9 | 129 | 294 | 267 |
| 95% Confidence Interval | 10 | 29 | 14 | 14 |
| Weight Loss, Wt % | 18.1 | 13.3 | 10.0 | 7.0 |
| 95% Confidence Interval | 0.51 | 0.47 | 0.39 | 0.45 |
| Retained Properties (7 days at 100° C., AC/hour) | | | | |
| Retained 100% Modulus Strength, % | N/A* | 125 | 170 | 141 |
| 95% Confidence Interval | N/A* | 1.4 | 0.6 | 0.4 |
| Retained Tensile Strength, % | 117 | 100 | 107 | 92 |
| 95% Confidence Interval | 1.0 | 0.4 | 0.2 | 0.2 |
| Retained Elongation, % | 3 | 38 | 87 | 73 |
| 95% Confidence Interval | 0.8 | 1.4 | 1.0 | 1.0 |
| Carbon Volatility (24 hours at 70° C.) | | | | |
| Mean (3 Specimens) | 1.9 | 1.5 | 1.2 | 0.6 |
| 95% Confidence Interval | 0.0 | 0.0 | 0.1 | 0.0 |
| Low Temperature | | | | |
| Clash Berg ($T_f$), ° C. | −16.0 | −12.0 | −10.0 | −21.0 |
| 95% Confidence Interval | 1.3 | 1.3 | 1.5 | 0.9 |
| QUV/Humid Aging (2 Wks/2 Wks) | yellow | yellow | dark yellow | v. good |

*Sample was too stiff to obtain results.

aromatic or saturated ring which may be the same or different, and the plasticizer compound is of the formula:

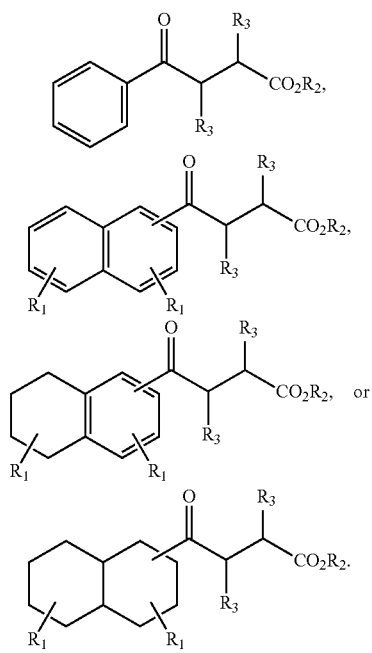

wherein $R_1$ is as set forth above, $R_2$ is the alkyl residue of the OXO-alcohols, and $R_3$ is H or $C_1$-$C_8$ linear or branched alkyl group.

3. The process according to claim 1 or 2, wherein the acylation is catalyzed by a heterogeneous catalyst, a mixed metal oxide or a Lewis acid.

4. The process according to any preceding claim, wherein the acylation is conducted using a stoichiometric amount of $AlCl_3$.

5. The process according to any preceding claim, further comprising hydrogenating the keto-group(s) of the plasticizer compound to form alcohol groups, and esterifying the alcohol groups with $C_4$ to $C_{13}$ linear or OXO-acids.

6. The process according to any preceding claim, further comprising hydrogenating one or more of the aromatic rings.

7. The process of any of claims 2-6, further comprising hydrogenating the keto-group(s) of the plasticizer compound to form alcohol groups, and esterifying the alcohol groups with $C_4$ to $C_{13}$ linear or OXO-acids to form plasticizer compounds of the formula:

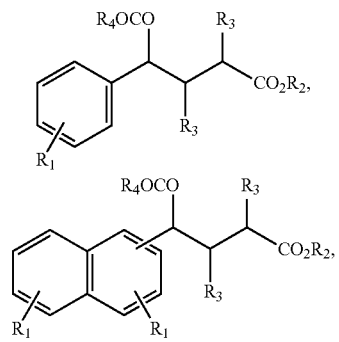

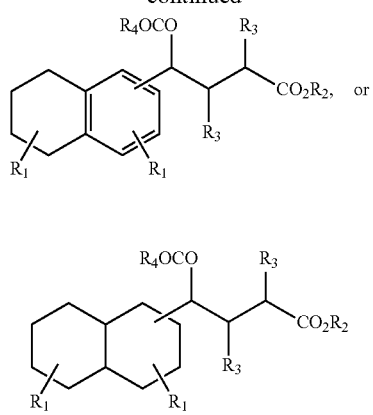

wherein $R_4$ is the alkyl residue of said linear or OXO-acids.

8. A plasticizer compound of the formula:

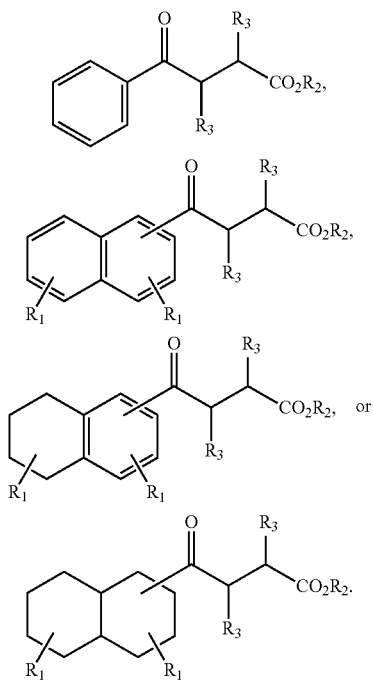

wherein $R_1$ is selected from the group consisting of H, $C_1$-$C_9$ linear or branched alkyl, cycloalkyl, or $C_1$-$C_4$ ether, $R_2$ is the alkyl residue of $C_4$ to $C_{13}$ OXO-alcohols and wherein there may be 1 or 2 $R_1$ groups present on the aromatic or saturated ring which may be the same or different, and $R_3$ is H or $C_1$-$C_8$ linear or branched alkyl group.

9. A plasticizer compound of the formula:

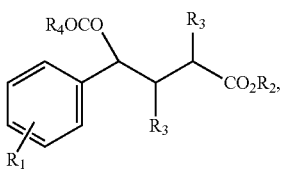

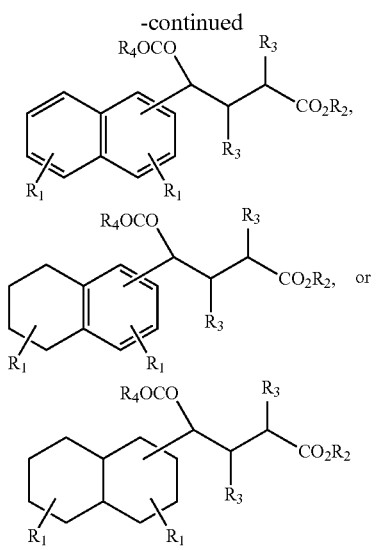

wherein $R_1$ is selected from the group consisting of H, $C_1$-$C_9$ linear or branched alkyl, cycloalkyl, or $C_1$-$C_4$ ether, wherein there may be 1 or 2 $R_1$ groups present on the aromatic or saturated ring which may be the same or different, $R_2$ is the alkyl residue of $C_4$ to $C_{13}$ OXO-alcohols, $R_3$ is H or $C_1$-$C_8$ linear or branched alkyl group, and $R_4$ is the alkyl residue of $C_4$ to $C_{13}$ linear or OXO-acids.

10. A composition comprising a polymer and a plasticizer of the formula:

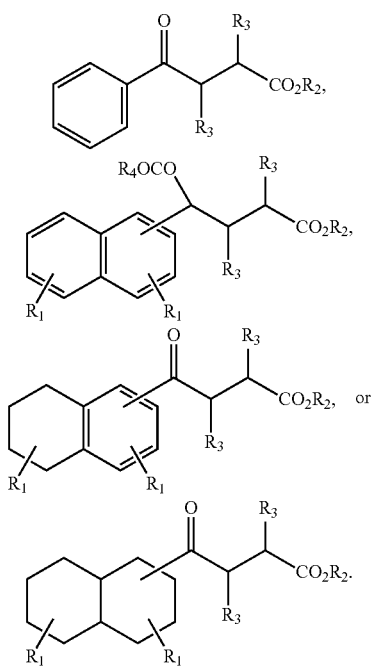

wherein $R_1$ is selected from the group consisting of H, $C_1$-$C_9$ linear or branched alkyl, cycloalkyl, or $C_1$-$C_4$ ether, wherein there may be 1 or 2 $R_1$ groups present on the aromatic or saturated ring which may be the same or different, $R_2$ is the alkyl residue of $C_4$ to $C_{13}$ OXO-alcohols, and $R_3$ is H or $C_1$-$C_8$ linear or branched alkyl group.

11. A composition comprising a polymer and a plasticizer of the formula:

wherein $R_1$ is selected from the group consisting of H, $C_1$-$C_9$ linear or branched alkyl, cycloalkyl, or $C_1$-$C_4$ ether wherein there may be 1 or 2 $R_1$ groups present on the aromatic or saturated ring which may be the same or different, $R_2$ is the alkyl residue of $C_4$ to $C_{13}$ OXO-alcohols, $R_3$ is H or $C_1$-$C_8$ linear or branched alkyl group, and $R_4$ is the alkyl residue of $C_4$ to $C_{13}$ linear or OXO-acids.

12. The composition of claims 10 or 11, wherein the polymer is selected from the group consisting of vinyl chloride resins, polyesters, polyurethanes, ethylene-vinyl acetate copolymer, rubbers, poly(meth)acrylics and combinations thereof.

13. The composition of claim 12, wherein the polymer is polyvinylchloride.

14. The composition of claim 10 or 11, wherein $R_2$ has an average branching of from 0.2 to 4.0 branches per group.

15. The composition of claim 11 or 14, wherein $R_4$ has an average branching of from 0.2 to 4.0 branches per group.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. The

What is claimed is:

1. A plasticizer compound of the formula:

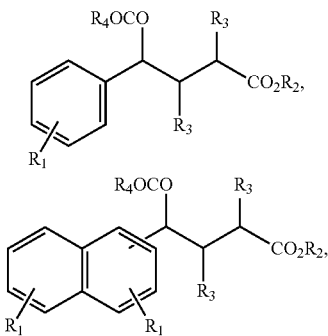

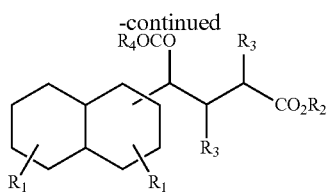

wherein $R_1$ is selected from the group consisting of H, $C_1$-$C_9$ linear or branched alkyl, cycloalkyl, or $C_1$-$C_4$ ether, and wherein there may be 1 or 2 $R_1$ groups present on the aromatic or saturated ring which may be the same or different, $R_2$ is the alkyl residue of $C_4$ to $C_{13}$ OXO-alcohols, $R_3$ is H or $C_1$-$C_8$ linear or branched alkyl group; and $R_4$ is the alkyl residue of $C_4$ to $C_{13}$ linear or OXO-acids.

2. The plasticizer compound of claim 1, wherein $R_2$ has an average branching of from 0.2 to 4.0 branches per group.

3. The plasticizer compound of claim 1, wherein $R_4$ has an average branching of from 0.2 to 4.0 branches per group.

4. The plasticizer compound of claim 1, wherein $R_2$ has an average branching of from 0.2 to 4.0 branches per group and $R_4$ has an average branching of from 0.2 to 4.0 branches per group.

* * * * *